United States Patent [19]
Malek et al.

[11] Patent Number: 5,665,545
[45] Date of Patent: Sep. 9, 1997

[54] TERMINAL REPEAT AMPLIFICATION METHOD

[75] Inventors: Lawrence Malek, Brampton; Roy Sooknanan, Toronto, both of Canada

[73] Assignee: Akzo Nobel N.V., Arnheim, Netherlands

[21] Appl. No.: 345,505

[22] Filed: Nov. 28, 1994

[51] Int. Cl.$^6$ ............................ C12Q 1/68; C12P 19/34
[52] U.S. Cl. ..................... 435/6; 435/91.2; 435/91.21; 435/91.5; 435/91.51; 435/91.52; 435/91.53
[58] Field of Search ................. 435/6, 91.2, 91.21, 435/91.5, 91.51, 91.52, 91.53

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91.2 |
| 5,130,238 | 7/1992 | Malek et al. | 435/91.2 |
| 5,169,766 | 12/1992 | Schuster et al. | 435/91.2 |
| 5,194,370 | 3/1993 | Berninger et al. | 435/6 |

(List continued on next page.)

FOREIGN PATENT DOCUMENTS

| | | |
|---|---|---|
| 0 427 073 A2 | 5/1991 | European Pat. Off. . |
| 0 427 074 A2 | 5/1991 | European Pat. Off. . |
| 0 534 345 | 3/1993 | European Pat. Off. . |
| 0 585 660 | 3/1994 | European Pat. Off. . |
| 4213 029 | 4/1993 | Germany . |

(List continued on next page.)

OTHER PUBLICATIONS

Breaker, R.R. and Joyce, G.F., "Emergence of a replicating species from an in vitro RNA evolution reaction," *Proc. Nat'l. Acad. Sci. USA* 91:6093–6097 (1994).

Hattori, M. and Sakaki, Y., "Dideoxy sequencing method using denatured plasmid templates," *Anal. Biochem* 152:232–238 (1986).

(List continued on next page.)

*Primary Examiner*—Kenneth R. Horlick
*Attorney, Agent, or Firm*—Burns, Doane, Swecker & Mathis L.L.P.

[57] ABSTRACT

This invention relates to a process for amplifying a specific nucleic acid sequence or its complement at a relatively constant temperature and without serial addition of reagents. The process provides in a single reaction medium an RNA polymerase, DNA polymerase, a ribonuclease that hydrolyses RNA of an RNA-DNA hybrid without hydrolysing single or double-stranded RNA or DNA, and ribonucleoside and deoxyribonucleoside triphosphates. The process then provides an RNA first template in the reaction medium. The RNA first template comprises a sequence complementary to a specific nucleic acid sequence, minus-sense sequences for a promoter and initiation site that are recognized by the RNA polymerase, and a 5'-terminal sequence that is complementary to at least the minus-sense sequence of the initiation site. Thus, the RNA first template has an inverted repeat sequence which could fold into a 5'-terminal stem-loop structure. The DNA polymerase uses the RNA first template to synthesize a DNA second template that together comprise an RNA-DNA hybrid. The DNA second template has plus-sense sequences of the promoter and the initiation site, and a 3'-terminal priming sequence that is complementary to the plus-sense sequence of the initiation site. The ribonuclease then hydrolyses an RNA which comprises the RNA-DNA hybrid, allowing the 3'-terminal priming sequence to hybridize to the plus-sense sequence of the initiation site in the DNA second template. The DNA polymerase then uses the DNA second template to synthesize the promoter by extending the 3'-terminal priming sequence of the DNA second template. The resulting partially double-stranded DNA has a promoter oriented toward the apex of a stem-loop structure. The RNA polymerase then recognizes the promoter and transcribes the DNA second template, thereby providing copies of the RNA first template. The process thereafter maintains the reaction conditions for a time sufficient to achieve a desired amplification of the specific nucleic acid sequence or its complement. This invention includes a kit containing the reagents of this invention.

22 Claims, 23 Drawing Sheets

U.S. PATENT DOCUMENTS

| | | | |
|---|---|---|---|
| 5,215,899 | 6/1993 | Dattagupta | 435/6 |
| 5,369,003 | 11/1994 | Reischl et al. | 435/6 |
| 5,399,491 | 3/1995 | Kacian et al. | 435/91.21 |
| 5,409,818 | 4/1995 | Davey et al. | 435/91.21 |
| 5,474,916 | 12/1995 | Reischl et al. | 435/91.2 |
| 5,532,126 | 7/1996 | Chu et al. | 435/6 |

FOREIGN PATENT DOCUMENTS

| | | |
|---|---|---|
| WO 91/02818 | 3/1991 | WIPO . |
| WO 91/18115 | 11/1991 | WIPO . |
| WO 91/18155 | 11/1991 | WIPO . |
| WO 92/18521 | 10/1992 | WIPO . |
| WO 93/09246 | 5/1993 | WIPO . |
| WO 93/12244 | 6/1993 | WIPO . |
| WO 93/17127 | 9/1993 | WIPO . |
| WO 94/03624 | 2/1994 | WIPO . |
| WO 94/20639 | 9/1994 | WIPO . |
| WO 94/29481 | 12/1994 | WIPO . |

OTHER PUBLICATIONS

Holmes, D.S. and Quigley, M., "A rapid boiling method for the preparation of bacterial plasmids," *Anal. Biochem.* 114:193–197 (1981).

Mullis et al., "Specific enzymatic amplification of DNA in vitro: The polymerase chain reaction," *Cold Spring Harbor Symp. Quant. Biol.* 51:263–273 (1986).

Saiki et al., "Primer-directed enzymatic amplification of DNA with a thermostable DNA polymerase," *Science* 239:487–491 (1988).

Sanger, et al., "DNA sequencing with chain-terminating inhibitors," *Proc. Nat'l Acad. Sci. USA* 74:5463–5467 (1977).

Kwoh et al., *Proc. Natl. Acad. Sci USA* 86, 1173–1177 (1989).

Kievits et al., *J. Virol. Meth.* 35, 273–286 (1991).

Guatelli et al., *Proc. Natl. Acad Sci USA* 87, 1874–1878 (1990).

Maniatis et al., "Molecular Cloning: A laboratory manual" *Cold Spring Harbor Laboratory* Cold Spring Harbor, NY p. 170 (1982).

Miller, J.H., "Experimentals in Molecular genetics" *Cold Spring Harbor Laboratory*, Cold Spring Harbor, NY p. 433 (1972).

A. Specific nucleic acid (RNA) sequence

```
         10         20         30         40         50
5'-AGACAAGAUA GAGGAAGAGC AAAACAAAAG UAAGAAAAAA GCACAGCAAG
         60         70         80         90        100
CAGCAGGGCA UGCAGGGCCU AUUGCACCAG GCCAGAUGAG AGAACCAAGG
        110        120        130   134
GGAAGUGACA UAGCAGGAAC UACUAGUACC CUUC-3'
```

B. Complementary DNA sequence

```
         10         20         30         40         50
5'-GAAGGGTACT AGTAGTTCCT GCTATGTCAC TTCCCCTTGG TTCTCTCATC
         60         70         80         90        100
TGGCCTGGTG CAATAGGCCC TGCATGCCCT GCTGCTTGCT GTGCTTTTT
        110        120        130   134
CTTACTTTTG TTTTGCTCTT CCTCTATCTT GTCT-3'
```

Figure 5

A. TRAM second primer sequence

```
          10         20         30         40         50
5'-GGGAGATTTA ACTCAGACGG GTGTTAAATC TCCCTATAGT GAGTCGTATT
          60         70       78
   AGAATTGAAG GGTACTAGTA GTTCCTGC-3'
```

B. NASBA™ second primer sequence

```
          10         20         30         40       48
5'-AATTCTAATA CGACTCACTA TAGGGAGAAG GGTACTAGTA GTTCCTGC-3'
```

C. First primer sequence

```
          10         20 21
5'-AGACAAGATA GAGGAAGAGC A-3'
```

Figure 6

A. First primer sequence (P2)

```
            10          20 21
5'-AGACAAGATA GAGGAAGAGC A-3'
```

B. First primer sequence (P2.1)

```
           10          20          30          40   44
5'-TACTCATGCT GAGTCCATGA GTAAGACAAG ATAGAGGAAG AGCA-3'
```

C. First primer sequence (P2.2)

```
         10          20          30
5'-TACTGAGTAA GACAAGATAG AGGAAGAGCA-3'
```

Figure 20

TERMINAL REPEAT AMPLIFICATION METHOD

FIELD OF THE INVENTION

This invention relates to a process for amplifying the number of copies of a specific nucleic acid sequence or its complement by using a template having a terminal sequence complementary to another sequence within the template.

BACKGROUND OF THE INVENTION

The presence of nucleic acids in a sample may indicate that a source from which the sample is taken has a disease, disorder or abnormal physical state. Certain diagnostics determine whether nucleic acids are present in a sample. These diagnostics invariably require amplification of nucleic acids because of the copy number problem. In a virus or cell, for example, there is usually a single copy of a particular gene. Without amplification of specific nucleic acids of the gene, it is often difficult to detect the presence of the nucleic acids.

One approach is to increase the copy number of the specific sequence, in preference to other sequences present in the sample, using an in vitro amplification method. The "polymerase chain reaction" (PCR) is one such technique (Mullis, K. et al., Cold Spring Harbor Symp. Quant. Biol. 52:263–273 (1986), Mullis, K., et al., U.S. Pat. No. 4,683,202) to selectively increase the copy number of a DNA segment having a particular sequence. In general, PCR involves treating the sample suspected of containing a target DNA sequence with oligonucleotide primers such that a primer extension product is synthesized by a DNA-dependent DNA polymerase. The primer extension product DNA strand is separated from the template strand in the preferred embodiment using heat denaturation. Both the original template and the primer extension product then serve as templates in the next and subsequent cycles of extension, resulting approximately in the doubling of the number of target DNA sequences in the sample at the end of each cycle. Consequently, multiple cycles result in the quasi-exponential amplification of the target nucleic acid sequence. Optimal practice of the PCR requires the use of a thermocycler capable of rapid changes of temperature and of a DNA polymerase, such as Taq polymerase (Saiki et al., Science 239:487–491 (1988) and Saiki, R. et al., U.S. Pat. No. 4,683,195) that resists the denaturation caused by repeated exposure to temperatures above 90° C. required to separate the DNA strands.

Another in vitro amplification method referred to as the T7RT method (Burg et al., U.S. Ser. No. 080,479, abandoned) uses an RNA polymerase in addition to a DNA polymerase (a reverse transcriptase) to increase the yield of products per cycle of amplification. The method involves the use of two primers, one of which contains a promoter for the synthesis of a double-strand DNA intermediate from an RNA product by a series of primer hybridization, primer extension and product denaturation steps. The double-stranded DNA intermediate containing a promoter derived from one of the primers which directs the synthesis of multiple copies of RNA which can be used for the synthesis of additional copies of the double-stranded DNA intermediate. Multiple cycles result in an exponential amplification. The yield of products per amplification cycle exceeds that of PCR by at least an order of magnitude, thus requiring fewer cycles to obtain the same overall level of amplification. The major drawback to the T7RT method is the inherent heat denaturation step which is necessary to separate the cDNA intermediate from the RNA product but inactivates both of the thermolabile enzymes used in the process. Consequently, fresh enzymes must be added to the reaction mixture at each cycle following the heat denaturation step.

U.S. Ser. No. 07/211,384, U.S. Pat. No. 5,409,818, of Cangene Corporation describes another amplification process known as NASBA™, which involves the use of two primers, one of which has a promoter, and three enzymes; an RNA polymerase, a DNA polymerase (a reverse transcriptase) and a ribonuclease (RNase H) that specifically degrades the RNA strand of an RNA-DNA hybrid. The cyclic process takes place at a relatively constant temperature throughout and without serial addition of reagents, wherein the first primer hybridizes to the RNA product, reverse transcriptase uses the RNA product as template to synthesize a DNA product by extension of the first primer, RNase H degrades the RNA of the resulting RNA-DNA hybrid, the second primer with the promoter hybridizes to the DNA product, reverse transcriptase uses the second primer as template to synthesize a double-stranded promoter by extension of the DNA product, an RNA polymerase uses the promoter and DNA product to transcribe multiple copies of the same RNA product. The unique addition of RNase H distinguishes NASBA™ from the T7RT process by eliminating the need for heat denaturation to separate the DNA product from its RNA template.

U.S. Pat. No. 5,130,238 of Cangene Corporation describes an enhanced nucleic acid amplification process known as enhanced NASBA™. The process is similar to that described in U.S. Ser. No. 07/211,384, and U.S. Pat. No. 5,409,818, and is enhanced by addition to the reaction mixture of an alkylated sulfoxide (for example, dimethyl sulfoxide) and BSA.

U.S. Ser. No. 08/275,250 of Cangene Corporation describes a further improvement of NASBA™. To overcome thermal denaturation during entry into the amplification cycle from DNA, this process of amplification uses RNA polymerase, specifically, *E. coli* RNA polymerase to eliminate the heating steps involved in entering the amplification cycle.

Notwithstanding these amplification processes, a need exists for improvements to the amplification process. It would be preferable if the amplification process required fewer steps and fewer manipulations by a user.

One step which would be helpful to eliminate is the addition of a promoter sequence to derived DNA to allow subsequent transcription. For example, it is known that DNA synthesis from a DNA or an RNA template requires a DNA or an RNA primer with a 3'-OH group. It is also known that normal synthesis of an RNA using T7 RNA polymerase requires a double-stranded DNA promoter immediately upstream of a template from which the RNA is transcribed. Such transcribed RNA would not contain a promoter sequence; thus one would need to add such promoter sequence to derived DNA to allow subsequent transcription. In NASBA™ and enhanced NASBA™ amplification reactions, these basic requirements are met by providing two primers, a first primer which hybridizes to the RNA product, and a second primer which has a plus-sense sequence of a T7 promoter and hybridizes to the DNA product. The first primer is extended using the RNA product as template to form the DNA product which serves as the template for transcription of the RNA product. The DNA product is extended using the second primer as template to form a double-stranded promoter for the transcription of the RNA product.

This invention improves upon NASBA™ and enhanced NASBA™ amplification reactions by reducing the number of primers required in the amplification cycle through the use of an RNA with an inverted repeat sequence at its 5'-end adjacent to a minus-sense sequence of the promoter recognized by an RNA polymerase. A cDNA copy of this RNA has an inverted repeat sequence at its 3'-end adjacent to a plus-sense sequence of a promoter. Upon removal of an RNA strand, the cDNA is capable of self-prig to form a partially double-stranded DNA stem-loop structure containing a double-stranded promoter oriented toward the apex of the stem-loop. Transcription of this DNA results in multiple copies of the same RNA with an inverted repeat sequence at its 5'-end adjacent to a minus-sense sequence of the promoter. Thus, the RNA product of the transcription encodes the minus-sense of the promoter sequence recognized by an RNA polymerase, and consequently the DNA copy of this RNA is fully functional as a template for transcription without the need for the addition of a promoter-bearing primer.

Other researchers have described the use of primers with inverted repeats or "hairpins" capable of transcription in nucleic acid amplification processes, namely, Dattagupta, N., EP 0 427 073 A2, and EP 0 427 074 A2, both published May 15, 1991. However, these hairpin primers encode plus-sense promoters that direct transcription of the target sequence without incorporating the sequence of the promoter itself into the product. Thus the processes described in these patents merely mimic the transcription phase of NASBA™ and enhanced NASBA™. Furthermore, these processes do not provide for cycling, that is, the generation of templates from products, except in ways which require participation by a user or mechanical intervention, and therefore the extent of amplification is limited.

Essentially the same process is described in Beringer, M., et al., WO 91/18155, published Nov. 28, 1991 except that the use of ribonuclease H is incorporated to enable cycling to occur. But, because the transcription products generated in this scheme do not carry promoter sequences, cycling still requires the presence of two primers, with the disadvantage that the first primer must encode both plus-sense and minus-sense strands of the promoter. In contrast, the first primer in NASBA™ and enhanced NASBA™ simply encode the plus-sense strand: the NASBA™ process provides for DNA synthesis to supply the minus strand.

Thus, a need exists for an amplification process which (1) eliminates the addition of a promoter sequence to derived DNA to allow subsequent transcription, (2) reduces the number of steps involved in the process, and (3) decreases the participation and manipulations by a user.

SUMMARY OF THE INVENTION

This invention is a method for amplifying a specific nucleic acid sequence, at a relatively constant temperature and without serial addition of reagents. This process comprises steps (A) through (C), which steps make the amplification more expedient, requiting less participation and manipulations by a user.

In step (A) one provides a single reaction medium containing reagents comprising an RNA polymerase, a DNA polymerase, ribonuclease that hydrolyses RNA of an RNA-DNA hybrid without hydrolysing single- or double-stranded RNA or DNA, and ribonucleoside and deoxyribonucleoside triphosphates.

In step (B), one provides an RNA first template in the reaction medium. The RNA first template comprises a sequence complementary to a specific nucleic acid sequence, minus-sense sequences for a promoter and an initiation site that are recognized by the RNA polymerase, and a 5'-terminal sequence that is complementary to the minus-sense sequence of the initiation site. An RNA first template is used to synthesize a DNA second template which comprises plus-sense sequences of the promoter and the initiation site, and a 3'-terminal priming sequence that is complementary to the plus-sense sequence of the initiation site. Thus, the DNA second template has an inverted repeat sequence which could fold into a 3'-terminal stem-loop structure for self-priming. The DNA second template is converted to a form containing a double-stranded promoter that is oriented toward the apex of the stem-loop structure. The form of DNA second template containing a double-stranded promoter is used to synthesize copies of the original RNA first template.

Thereafter, a cycle ensues where the DNA polymerase uses the RNA first template to synthesize a DNA second template, the ribonuclease hydrolyses RNA of the RNA-DNA hybrid, the 3'-terminal priming sequence hybridizes to said plus-sense sequence of said initiation site, DNA polymerase uses the DNA second template to synthesize the double-stranded promoter, the RNA polymerase recognizes the promoter and transcribes the DNA second template, thereby providing copies of the RNA first template.

In step (C), one maintains the conditions for the reaction for a time sufficient to achieve desired amplification of the specific nucleic acid sequence.

In one embodiment of this invention, the reaction medium and cycle further comprise a first oligonucleotide primer that hybridizes to the RNA first template and is extended using the DNA polymerase to synthesize a DNA second template (FIG. 1A). In one aspect of this embodiment, the first oligonucleotide primer further comprises a 5'-self-complementary sequence such that the RNA polymerase uses the 5'-self-complementary sequence of the first oligonucleotide primer as template to transcribe an RNA first template with a 3'-self-complementary sequence (FIG. 1B).

The cycle is shown in FIG. 1A and FIG. 1B. The steps leading up to the cycle of FIG. 1A (FIG. 2, FIG. 3, FIG. 4), could also be used to lead up to the cycle of FIG. 1B, except that the first primer would have a stem loop on its 5'-end.

There are a number of ways to provide the RNA first template of step (B). In one embodiment (FIG. 2), one provides in the reaction medium a single-stranded RNA comprising the specific nucleic acid sequence, and adds to the reaction medium a DNA ligase, a first oligonucleotide primer and a second oligonucleotide primer further comprising a 5'-terminal phosphate, such that; the second oligonucleotide primer hybridizes to the single-stranded RNA; the DNA polymerase uses the single-stranded RNA as a template to synthesize a complementary DNA by extending the second oligonucleotide primer and thereby forms an RNA-DNA hybrid; the ribonuclease hydrolyses the RNA which is part of the RNA-DNA hybrid; the first oligonucleotide primer hybridizes to the complementary DNA; the DNA polymerase uses the complementary DNA as template to synthesize a DNA segment which terminates at the second oligonucleotide primer by extending the first oligonucleotide primer; the DNA ligase joins the DNA segment to the second oligonucleotide primer and thereby forms a DNA second template, and the RNA polymerase recognizes the promoter and transcribes the DNA second template, thereby providing copies of the RNA first template. In one aspect of this embodiment, one adds the single-stranded RNA to the reaction medium. In another aspect of this embodiment, one adds to the reaction medium a DNA comprising a promoter and a complementary DNA template, such that the RNA polymerase transcribes the complementary DNA thereby providing copies of the single-stranded RNA.

In another embodiment, one also provides a stem loop on the 5'-end of the first primer.

In another embodiment, one provides the RNA first template of step (B) by adding to the reaction medium a DNA ligase, a first oligonucleotide primer and a single-stranded DNA which comprises a sequence complementary to the specific nucleic acid sequence and a 5'-terminal second oligonucleotide primer sequence further comprising a 5'-terminal phosphate, such that; the first oligonucleotide primer hybridizes to the single-stranded DNA; the DNA polymerase uses the single-stranded DNA as template to synthesize a DNA segment which terminates at the 5'-terminal sequence of the stem loop structure of the single-stranded DNA by extending the first primer; the DNA ligase joins the DNA segment to the 5'-terminal sequence of the single-stranded DNA and thereby forms a DNA second template; and the RNA polymerase recognizes the promoter and transcribes the DNA second template thereby providing copies of the RNA first template. In one aspect of this embodiment, one adds an RNA-DNA hybrid comprising the single-stranded DNA such that the ribonuclease hydrolyzes RNA which is part of the RNA-DNA hybrid.

In another embodiment, one provides the RNA first template of step (B) by providing in the reaction medium a single-stranded RNA comprising the specific nucleic acid sequence, a first oligonucleotide primer and a second oligonucleotide primer further comprising a 5'-terminal oligoribonucleotide segment, such that; the second oligonucleotide primer hybridizes to the single-stranded RNA; the DNA polymerase uses the single-stranded RNA as a template to synthesize a complementary DNA by extending the second oligonucleotide primer and thereby forms an RNA-DNA hybrid; the ribonuclease hydrolyzes RNA which is part of the RNA-DNA hybrid; the first oligonucleotide primer hybridizes to the complementary DNA, the DNA polymerase uses the complementary DNA and second primer as template to synthesize a DNA second template by extension of the first oligonucleotide primer and thereby forms an RNA-DNA hybrid in the oligoribonucleotide segment of the second primer; the ribonuclease hydrolyzes the oligoribonucleotide segment of the second primer, allowing the 3'-terminal priming sequence to hybridize to the plus-sense sequence of the initiation site in the DNA second template; the DNA polymerase uses the DNA second template to synthesize the promoter by extending the DNA second template; and the RNA polymerase recognizes the promoter and transcribes the DNA second template, thereby providing copies of the RNA first template. In one aspect of this embodiment, one adds the single-stranded RNA to the reaction medium. In another aspect of this embodiment, one adds to the reaction medium a DNA comprising a promoter and a complementary DNA template, such that the RNA polymerase transcribes the complementary DNA thereby providing copies of the single-stranded RNA.

In another embodiment, one provides the RNA first template of step (B) by adding to the reaction medium a first oligonucleotide primer and a single-stranded DNA which comprises a sequence complementary to the specific nucleic acid sequence and a 5'-terminal second oligonucleotide primer sequence further comprising a 5'-terminal oligoribonucleotide segment, such that; the first oligonueleotide primer hybridizes to the single-stranded DNA; the DNA polymerase uses the single-stranded DNA and second oligonucleotide primer as template to synthesize a DNA second template by extension of the first oligonucleotide primer and thereby forms an RNA-DNA hybrid in the 5'-terminal oligoribonucleotide segment of the second primer; the ribonuclease hydrolyzes the oligoribonucleotide segment of the second primer, allowing the 3'-terminal priming sequence to hybridize to the plus-sense sequence of the initiation site in the DNA second template; the DNA polymerase uses the DNA second template to synthesize the promoter by extending the DNA second template; and the RNA polymerase recognizes the promoter and transcribes the DNA second template thereby providing copies of the RNA first template. In one aspect of this embodiment, one adds an RNA-DNA hybrid comprising the single-stranded DNA such that the ribonuclease hydrolyses the RNA which is part of the RNA-DNA hybrid.

In another embodiment, one provides the RNA first template of step (B) by adding to the reaction medium a first oligonucleotide primer, and by providing in the reaction medium a single-stranded RNA which comprises the RNA first template such that; the first oligonucleotide primer hybridizes to the single-stranded RNA; the DNA polymerase uses the single-stranded RNA template to synthesize a DNA second template by extension of the first oligonucleotide primer and thereby forms an RNA-DNA hybrid; the ribonuclease hydrolyzes RNA which comprises the RNA-DNA hybrid, allowing the 3'-terminal priming sequence to hybridize to the plus-sense sequence of the initiation site in the DNA second template; the DNA polymerase uses the DNA second template to synthesize the promoter by extending the DNA second template; and the RNA polymerase recognizes the promoter and transcribes the DNA second template thereby providing copies of the RNA first template. In one aspect of this embodiment, one adds the single-stranded RNA to the reaction medium. In another aspect of this embodiment, one adds to the reaction medium a DNA comprising a promoter and a DNA second template, such that the RNA polymerase transcribes DNA second template thereby providing copies of the single-stranded RNA.

In another embodiment, one provides the RNA first template of step (B) by adding to the reaction medium a single-stranded DNA which comprises a sequence of the specific nucleic acid comprising a DNA second template; such that the 3'-terminal priming sequence hybridizes to the plus-sense sequence of the initiation site of the single-stranded DNA; the DNA polymerase uses the single-stranded DNA as template to synthesize a promoter by extension from its 3' terminus; and the RNA polymerase recognizes the promoter and transcribes the single-stranded DNA thereby providing copies of the RNA first template.

In another embodiment, the process comprises a step (D) of monitoring the reaction medium for consumption of any of the reagents used in the reaction or for the accumulation of any product of the amplification cycle.

In another embodiment, step (D) includes comparing the consumption of a reagent or accumulation of the product of the cycle with a control cycle in which the specific nucleic acid sequence or its complement is absent.

DEFINITIONS

In this application, unless the context requires otherwise:

| | |
|---|---|
| "AMV" | means avian myeloblastosis virus. |
| "ATP" | means adenosine triphosphate. |
| "CTP" | means cytosine triphosphate. |
| "complementary" | means that two nucleic acids are capable of hybridization, under given conditions of ionic strength and temperature. |
| "self complementary" | means complementary within a single sequence. |
| "dATP" | means deoxyadenosine triphosphate. |
| "dCTP" | means deoxycytosine triphosphate. |
| "dGTP" | means deoxyguanosine triphosphate. |
| "dTTP" | means deoxythymine triphosphate. |
| "GTP" | means guanosine triphosphate. |
| "ITP" | means inosine triphosphate. |
| "KCl" | means potassium chloride. |
| "MgCl$_2$" | means magnesium chloride. |
| "NASBA ™" | means nucleic acid based amplification as described in United States Ser. No. 07/211,384 and corresponding patents and applications. |
| "enhanced NASBA ™" | means enhanced nucleic acid amplification as described in U.S. Pat. No. 5,130,238 and corresponding patents and applications. |
| "specific nucleic acid sequence" | means a sequence of single-stranded or double-stranded nucleic acids or a sequence complementary to such sequence which one wishes to amplify. |
| "TRAM ™" | means terminal repeat amplification method, the method of this invention. |
| "Tris-HCl" | means Tris hydrochloride. |
| "UTP" | means uridine triphosphate. |
| "terminal priming sequence" | means a terminal sequence that is self-complementary. |

BRIEF DESCRIPTION OF DRAWINGS AND FIGURES

In drawings and figures which illustrates embodiments of the invention,

FIGS. 5A and 5B show the specific nucleic acid sequence (RNA (SEQ ID NO: 2) and cDNA (SEQ ID NO: 3) that was amplified.

FIGS. 6A–6C shows the nucleic acid sequences of the TRAM second primer (SEQ ID NO: 4), the NASBA™ second primer (SEQ ID NO:5) and the first primer for both NASBA™ and TRAM (SEQ ID NO: 6).

FIGS. 20A–20C show the nucleotide sequences of the first primer (P2) (SEQ ID NO: 8) and two alternative first primers (P2.1 (SEQ ID NO:9) and P2.2SEQ ID NO: 10) containing 5'-terminal stem-loop structures.

DETAIL DESCRIPTION OF PREFERRED EMBODIMENT

Figure 1A:
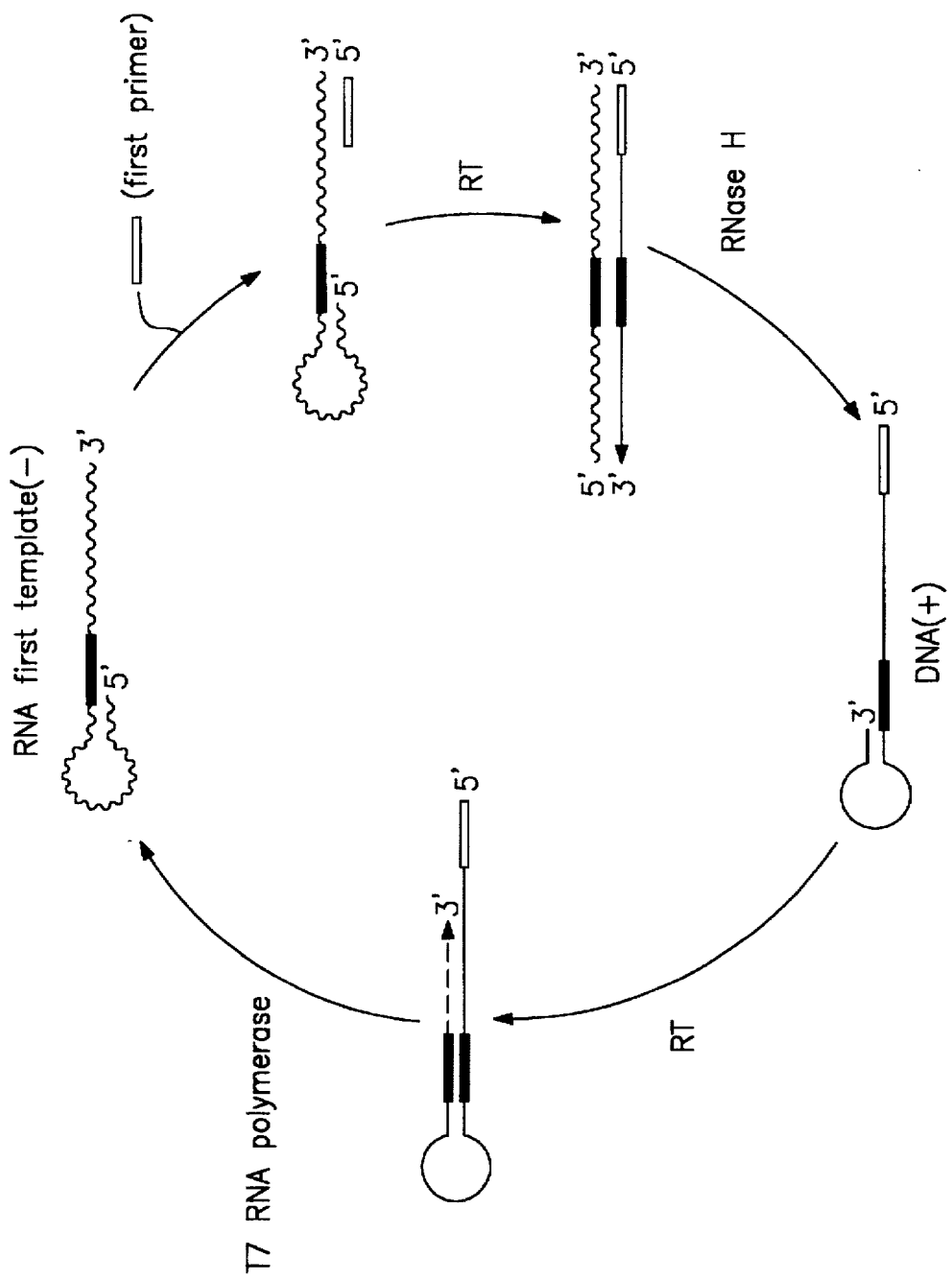
FIG. 1A is a general illustration of the cyclic amplification process for TRAM starting from an RNA first template and a first primer.
Figure 1B:
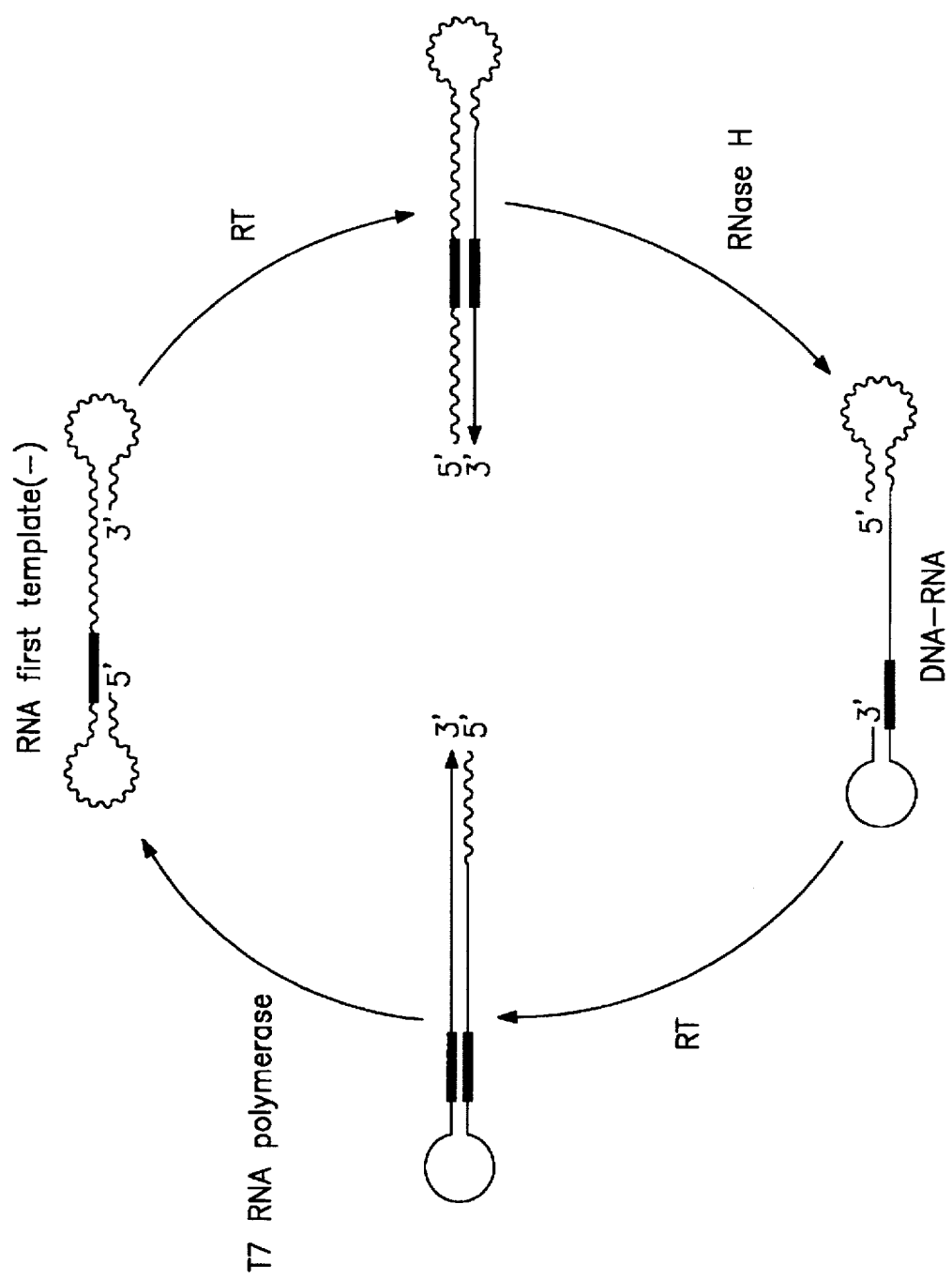
FIG. 1B is a general illustration of the cyclic amplification process for TRAM starting from an RNA first template and independent of primers.

In this invention, an RNA first template and DNA second template are alternately used for the synthesis of one from the other in the cyclic processes illustrated in FIG. 1A and FIG. 1B.

This invention is a method for amplifying a specific nucleic acid sequence, at a relatively constant temperature and without serial addition of reagents. This process comprises steps (A) through (C) , which steps make the amplification more expedient, requiring less participation and manipulations by a user.

In step (A) one provides a single reaction medium containing reagents comprising an RNA polymerase, a DNA polymerase, ribonuclease that hydrolyses RNA of an RNA-DNA hybrid without hydrolysing single- or double-stranded RNA or DNA, and ribonucleoside and deoxyribonucleoside triphosphates.

In the preferred embodiment of the cyclic amplification process, the reaction medium further comprises a single primer (the first oligonucleotide primer), which contains a sequence that hybridizes to the first RNA template and is used in the cyclic amplification process, as shown in FIG. 1A. The RNA first template is used to synthesize the DNA second template by hybridizing the first oligonucleotide primer to the RNA first template, and by synthesizing a complementary DNA second template by extension of the first oligonucleotide primer using the DNA polymerase.

In another embodiment of the cyclic amplification process, the RNA first template further comprises a 3'-terminal priming sequence that can be extended by using the DNA polymerase to synthesize a DNA second template, as shown in FIG. 1B.

In either process, the DNA second template is separated from the RNA first template of the resulting RNA-DNA hybrid by, for example, hydrolysis of the RNA by using a ribonuclease which is specific for RNA-DNA hybrids (for example, ribonuclease H). The DNA second template is converted to a form containing a double-stranded promoter by hybridizing its 3'-terminal priming sequence to the plus-sense sequence of the initiation site of the DNA second template and by synthesizing the minus-sense sequence of the promoter by extension of the 3'-terminal priming sequence using the DNA polymerase. The form of DNA second template containing the double-strand promoter is used to synthesize copies of the RNA first template by using the RNA polymerase which recognizes the promoter and transcription initiation site defined in the RNA first template and in the DNA second template. Each newly synthesized RNA first template can be used to synthesize a DNA second template, which can be used to synthesize further copies of the RNA first template by repeating the cycle. In addition, repetition of the cycle does not require participation or manipulation by the user.

The amplification process involves the consumption of precursors (primers, ribonucleoside triphosphates and deoxyribonucleotide triphosphates) and the net accumulation of products (RNA and DNA). The processes of RNA and DNA synthesis will proceed non-synchronously until sufficient levels of nucleic acids have been synthesized to allow detection. The amplification process may be monitored by, for example, the synthesis of a labelled product from a labelled precursor. The possible detection schemes useful to the application of the amplification process are set out in U.S. Pat. No. 5,130,238 of Cangene Corporation.

The amplification process commences with the addition of a suitable template nucleic acid to the appropriate enzymes, primers and co-factors under the appropriate reaction conditions. This template nucleic acid is in a form which is capable of homogenous and continuous amplification and can function as an intermediate in the cycle set forth in FIG. 1A and FIG. 1B. The template nucleic acid could be a single-stranded RNA which comprises an RNA first template at its 5' terminus or a single-stranded DNA which comprises a DNA second template at its 3' terminus. The added template nucleic acid could also be an antecedent to the single-stranded RNA or DNA templates. For example, one could add to the reaction medium DNA comprising a promoter and a DNA second template, such that the RNA polymerase transcribes the DNA second template, thereby providing copies of the single-stranded RNA, which comprise an RNA first template at its 5' terminus. Alternatively, one could add an RNA-DNA hybrid comprising the single-stranded DNA such that the ribonuclease hydrolyzes RNA, thereby providing a copy of the single-stranded DNA which comprises a DNA second template at its 3' terminus.

The DNA second template which may be added to the reaction medium typically comprises plus-sense sequences of a promoter and an initiation site, and a 3'-terminal priming sequence that hybridizes to the initiation site. For certain applications, the DNA which is added to the reaction medium may comprise a mixture of synthetic oligonucleotides, in which the plus-sense sequences of the promoter may be partially or completely replaced with a partially or completely degenerate sequence. For example, the 17-base sequence preceding the transcription initiation site may be synthesized using an equimolar mixture of each of the four blocked deoxynucleoside phosphoramidites. From the mixture of added DNA template, only those comprising a functional promoter may be transcribed into an RNA product comprising the minus-sense sequence of the functional promoter. The RNA product can be amplified, by successive reverse transcription into the DNA product, followed by transcription of the DNA into the RNA product, until sufficient RNA and DNA products are synthesized to enable sequence determination. This application of the invention could be used to find the optimum promoter for a given RNA polymerase. The promoter sequence which is selected depends on the particular RNA polymerase which is used in the amplification reaction. The RNA polymerase may be natural, e.g. one encoded by bacteriophages T7, T3, sp6, K11 and BA14, or altered by chemical or genetic methods. This application of the invention should enable the determination of the promoter sequence for an RNA polymerase whose recognition sequence is unknown, or an RNA polymerase which has been altered at its natural promoter recognition site. This application of the invention could also be used to optimize the TRAM process by positioning the degenerate sequences at potentially important sites in the DNA template. Exhaustive amplification should result in the most effectively amplified sequence as the dominant product. Potentially important sites would include the sequence upstream of the promoter, the promoter, the initiation site, and the stem and loop.

In the primer-dependent amplification process, as shown in FIG. 1A, the RNA first template comprises the sequence information sufficient for its own transcription. In the primer-independent process, as shown in FIG. 1B, the RNA first template further comprises the sequence information sufficient for its own replication. This specialized sequence information is generally not initially present on a specific nucleic acid sequence that one wishes to amplify, and must be added to the RNA first template prior to the cyclic amplification process. An RNA first template could be transcribed from a DNA comprising a DNA second template which could be synthesized from the specific nucleic acid sequence using for example, oligonucleotide primers comprising the sequences required for transcription and replication of the RNA first template.

The first oligonucleotide primer, used in the preferred embodiment of the process as shown in FIG. 1A, comprises a 3'-terminal priming sequence which has a particular length and base composition to allow specific and efficient hybridization to the RNA first template and synthesis of the DNA second template, under the given conditions of ionic strength and temperature. In addition, the same first oligonucleotide primer is used in the preferred mode of providing an RNA first template in the reaction medium, wherein the first oligonucleotide primer hybridizes to DNA complementary to the specific nucleic acid sequence and is extended to synthesize the DNA second template, under the same conditions of ionic strength and temperature. It is contemplated that the first oligonucleotide primer may be composed partially or completely of nucleotides or nucleotide analogs other than the natural nucleotides. The first oligonucleotide primer may contain a 5'-terminal sequence which is unrelated to either the specific nucleic acid sequence or its complement. In one embodiment, the 5-terminal unrelated sequence provides a template for the transcription of an RNA first template further comprising a 3'-terminal self-complementary sequence, as shown in FIG. 1B. For this example, the 5'-terminal sequence may be complementary to another sequence of the same first oligonucleotide primer such that a 5'-terminal stem-loop structure could be formed. Alternatively, the 5'-terminal unrelated sequence or its transcribed RNA complement may hybridize to a nucleic acid which can be immobilized, or to which can be bound a useful non-nucleic acid component, such as a reporter to facilitate detection.

Although the preparation of a template nucleic acid is not part of the amplification process, the description of possible schemes for generating template nucleic acids may be useful to the application of the amplification process. It should be understood that the schemes which may be used for obtaining the template nucleic acid are not limited to the alternatives which are described herein, and it is contemplated that other methods may be used.

The preferred mode of providing an RNA first template in the reaction medium further utilizes a second oligonucleotide primer comprising a 3'-terminal priming sequence that is complementary to the specific nucleic acid sequence, a minus-sense sequence of a promoter, a minus-sense sequence of an initiation site and a 5'-terminal sequence that is complementary to the minus-sense sequence of the initiation site. The 3'-terminal priming sequence of the second oligonucleotide primer has a particular length and base composition to allow specific and efficient hybridization to the specific nucleic acid sequence and synthesis of a complementary DNA, under the given conditions of ionic strength and temperature. The minus-sense sequences of the promoter and initiation site when used as a template for synthesis of the plus-sense sequence of the promoter contain sufficient information to allow specific and efficient binding of an RNA polymerase and initiation of transcription at the desired site. The promoter sequence may be derived from the minus-sense strand of a natural promoter and initiation site. In a preferred embodiment, the second oligonucleotide primer comprises the sequence 5'-TCTCCCTATAGTGAGTCGTATTA-3', (SEQ. ID. NO. 1), which contains the minus-sense sequences of the initiation site and promoter for T7 RNA polymerase.

Alternatively, the initiation site and promoter for another phage RNA polymerase may be used. The 5'-terminal sequence of the second oligonucleotide primer has a particular length and base composition such that, the 3'-terminal priming sequence of the derived DNA second template can hybridize to the plus-sense sequence of the transcriptional initiation site and be extended to append a minus-sense sequence of a transcriptional promoter. The sequence between the 5'-terminal sequence and the minus-sense sequence of the initiation site on the second oligonucleotide primer has a particular length and composition, to allow transcription from the derived DNA comprising a DNA second template, under the given conditions of ionic strength and temperature. In addition, sequences which are unrelated to the promoter function may be included in the second oligonucleotide primer between the minus-sense sequence of the promoter and the 3'-terminal priming sequence which hybridizes to the specific nucleic acid sequence. It is contemplated that the second primer may be composed partially or completely of nucleotides or nucleotide analogs other than the natural oligonucleotides.

The preferred mode of providing an RNA first template involves adding to the reaction medium a DNA ligase and a second oligonucleotide primer that further comprises a 5'-terminal phosphate. It is contemplated that the 5'-terminal phosphate of the second oligonucleotide primer could be provided in the reaction medium by the addition to the reaction medium of an enzyme, such as polynucleotide kinase, that utilizes ATP from the reaction medium to phosphorylate the 5'terminus of the second oligonucleotide primer. It is also contemplated that other groups, for example, adenosine-5'-diphosphate may replace the phosphate at the 5' terminus of the second oligonucleotide primer. Indeed an oligonucleotide of the formula, A(5')pp(5') [second oligonucleotide primer], is the expected intermediate that is provided in the reaction medium by DNA ligase when acting upon its substrates ATP (or NAD) and the 5'-phosphorylated second oligonucleotide primer. It is further contemplated that A(5')pp(5')[second oligonucleotide primer] may be added to the reaction medium in preference to the 5'-phosphorylated second oligonucleotide primer. The DNA ligase may be any enzyme capable of joining the 3'terminus of a DNA segment to the 5'terminus of the second oligonucleotide primer. In the preferred mode, the T4 DNA ligase is used. In addition, other DNA ligases selected from prokaryotic or eukaryotic cells may be used. It is recognized that the use of some of these DNA ligases, for example those from *Escherischia coli* or *Thermus aquaticus*, would require the addition of NAD to the reaction medium, as a substrate for the DNA ligase.

Figure 2:
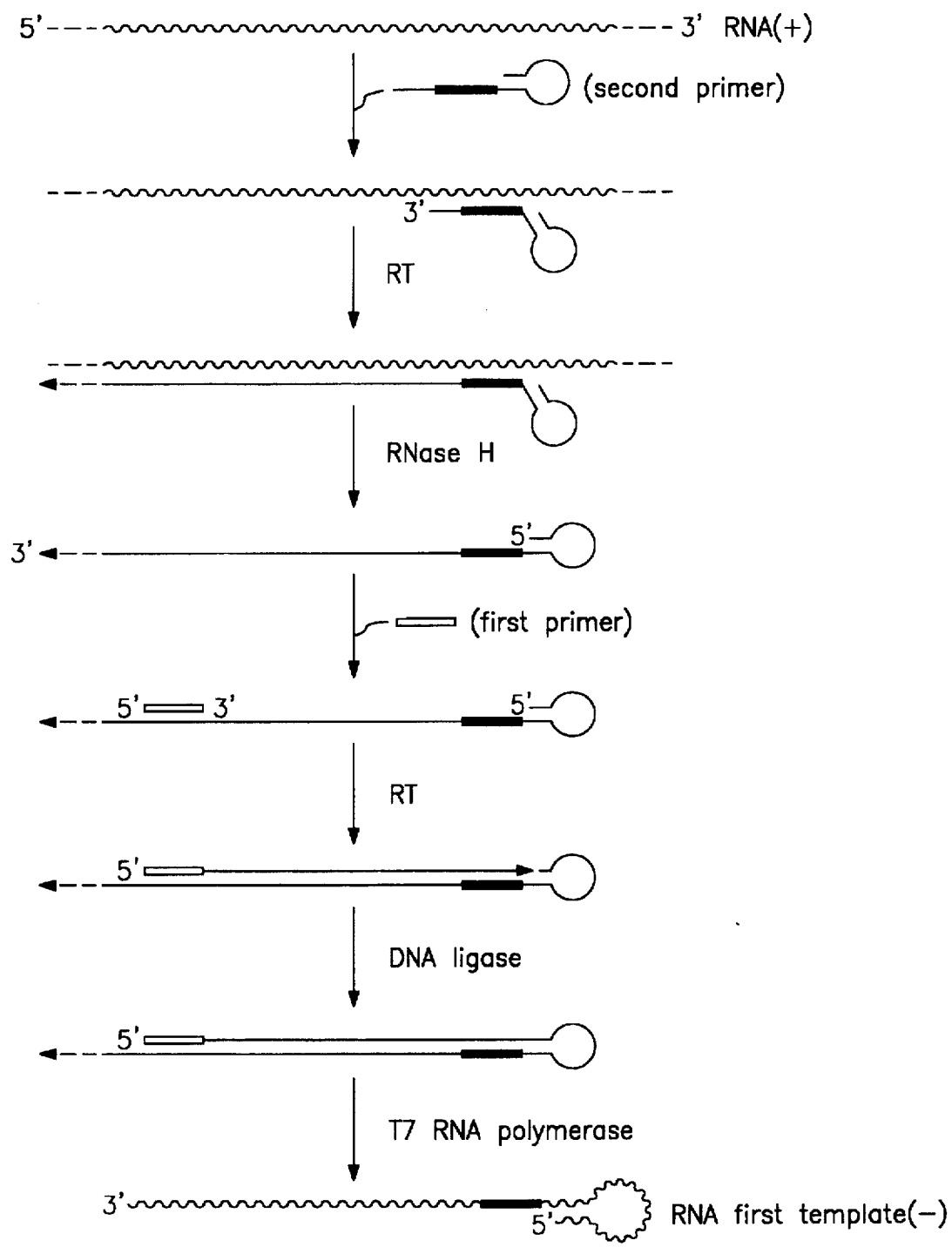
FIG. 2 is a general illustration of the steps required to generate an RNA first template starting from a specific RNA sequence using first and second primers comprising only deoxyribonucleosides.

Starting from RNA, the preferred mode of providing an RNA first template involves adding to the reaction medium a single-stranded RNA comprising the specific nucleic acid sequence, a DNA ligase and a second oligonucleotide primer with a 5'-terminal phosphate. (FIG. 2). The second oligonucleotide primer hybridizes to the single-strand RNA, and the DNA polymerase uses the single-stranded RNA as a template to synthesize a complementary DNA by extending the second oligonucleotide primer, thereby forming an RNA-DNA hybrid. The ribonuclease hydrolyzes an RNA which is part of the RNA-DNA hybrid to liberate the single-stranded complementary DNA which comprises a sequence complementary to the specific nucleic acid sequence, minus-sense sequences of the promoter and the initiation site wherein the 5'-terminal sequence is self-complementary to the minus-sense sequence of the initiation site, and a 5'-terminal phosphate (FIG. 2).

The first oligonucleotide primer hybridizes to the complementary DNA, and the DNA polymerase uses the complementary DNA as template to synthesize a DNA segment which terminates at the second oligonucleotide primer by extending the first oligonucleotide primer. The DNA ligase then joins the 3'terminus of the DNA segment to the 5'terminus of the oligonucleotide primer, thereby forming a DNA comprising a DNA second template. Finally, an RNA polymerase recognizes the promoter and transcribes the DNA second template, thereby providing copies of the RNA first template. (FIG. 2).

Figure 3:
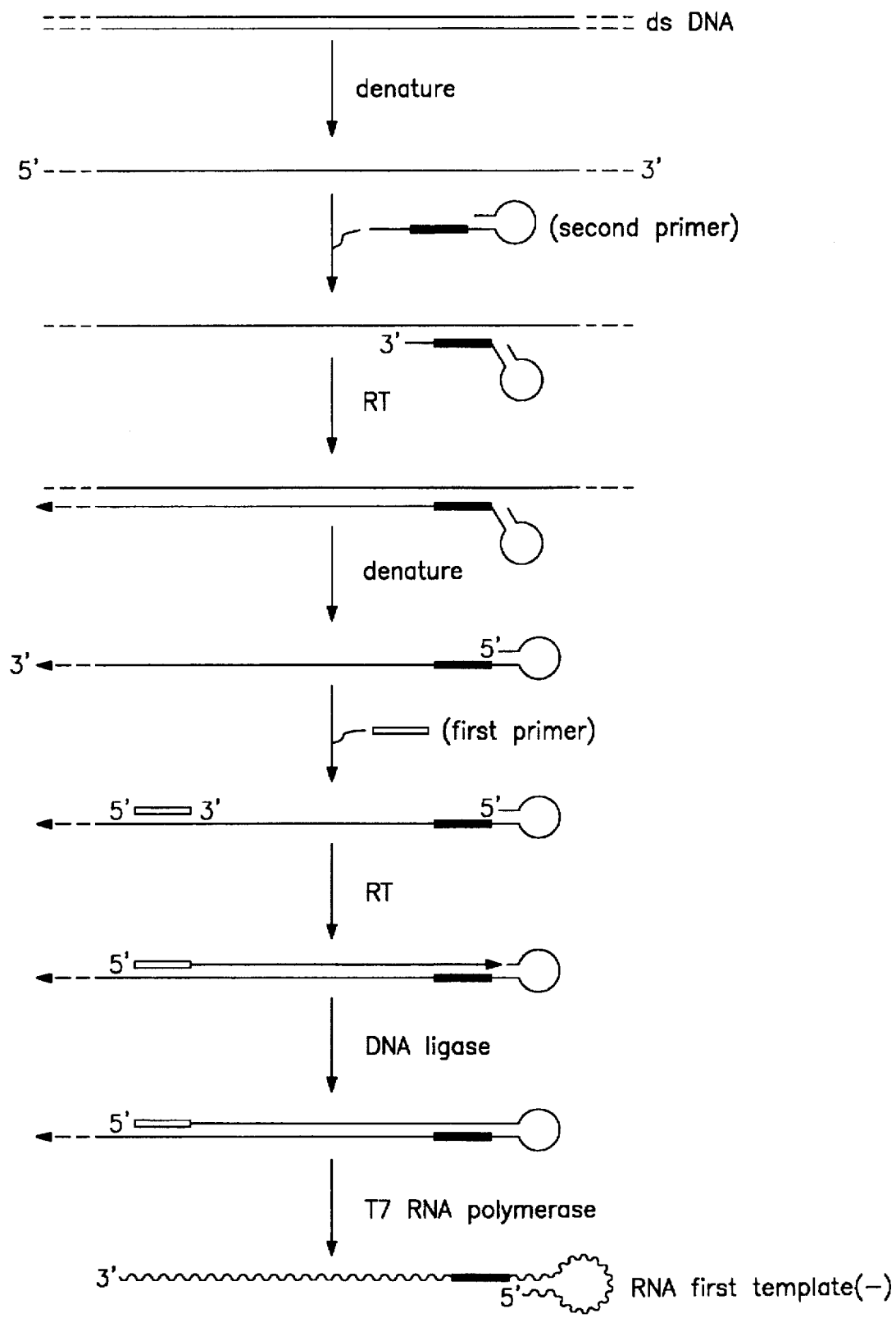
FIG. 3 is a general illustration of the steps required to generate an RNA specific first template starting from a double-stranded DNA sequence using first and second primers comprising only deoxyribonucleosides.

Starting from DNA, the preferred mode of providing an RNA first template involves adding to the reaction medium the DNA ligase and the single-stranded complementary DNA which comprises a sequence complementary to the specific nucleic acid sequence, minus-sense sequences of the promoter and the initiation site, a 5'-terminal sequence that is complementary to the minus-sense sequence of the initiation site, and a 5'-terminal phosphate. The single-stranded complementary DNA may be generated from a single-stranded DNA comprising the specific nucleic acid sequence (FIG. 3). In a separate process the single-stranded DNA is first separated from any DNA duplex by thermal or chemical denaturation. The second oligonucleotide primer hybridizes to the single-stranded DNA, and a DNA polymerase uses the single-stranded DNA as a template to synthesize a complementary DNA by extending the second oligonucleotide primer. The single-stranded complementary DNA is finally separated from the single-stranded DNA by thermal or chemical denaturation, and then added to the reaction medium along with the DNA ligase. In the reaction medium, the complementary DNA is used to provide copies of the RNA first template by the preferred mode set forth starting from RNA. (FIG. 3).

In addition to the single-stranded complementary DNA, any other nucleic acid intermediate set forth in the preferred mode starting from an RNA may be added to the reaction medium to provide an RNA first template. For example, one could add to the reaction medium the DNA ligase and an RNA-DNA hybrid comprising the single-stranded complementary DNA, such that the ribonuclease hydrolyses the RNA thereby providing a copy of the single-stranded complementary DNA. Alternatively an antecedent to one of the nucleic acid intermediates set forth in the preferred mode starting from an RNA may be added to the reaction medium to provide an RNA first template. For example, one could add to the reaction medium a DNA comprising a promoter, such that RNA polymerase recognizes the promoter and transcribes the DNA, thereby providing copies of the single-stranded RNA. The RNA and its antecedent DNA may be the products of an amplification process, for example NASBA™.

An alternative mode of providing an RNA first template in the reaction medium involves adding a second oligonucleotide primer that further comprises ribonucleotides from the 5' terminus preferably, through to beyond the minus-sense sequence of the initiation site, or possibly, through to beyond the minus-sense sequence of the promoter, or throughout the entire sequence of the primer to the 3' terminus. The second oligonucleotide may further comprise nucleoside substitutions, for example riboinosine for riboguanosine and ribocytosine for ribouridine, such that a 5'-terminal stem-loop structure would not be stable in the reaction medium, but under the same conditions, the 3' terminus of a complementary DNA synthesized using the second primer as template would hybridize to itself and prime DNA synthesis.

Figure 4:
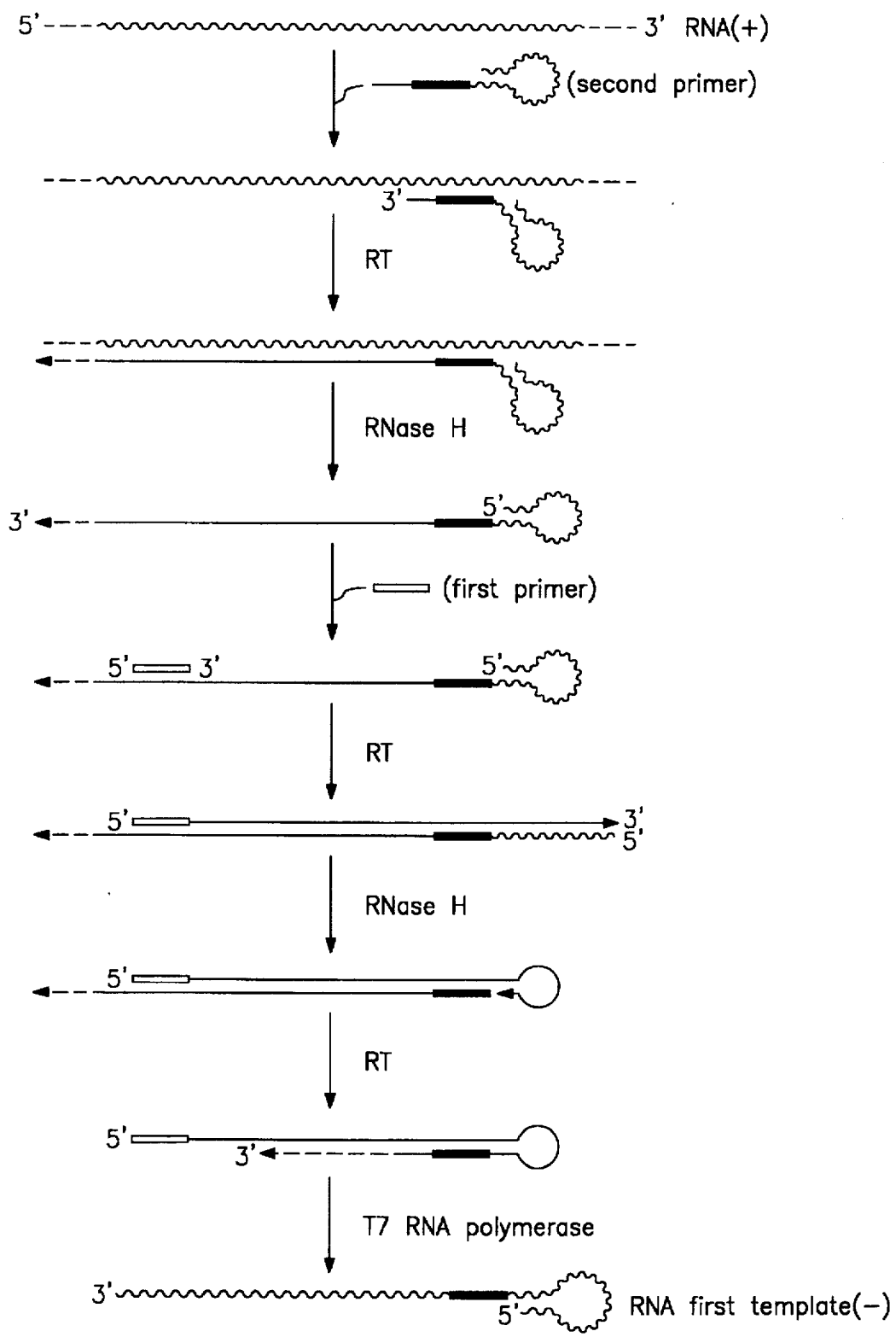
FIG. 4 is a general illustration of the step required to generate an RNA first template starting from a specific RNA sequence using a first primer comprising deoxyribonucleosides and a second primer comprising a mixture of deoxyribonucleosides and ribonucleosides.

An RNA first template may be provided by adding to the reaction medium a single-stranded RNA comprising a specific nucleic acid sequence and a second oligonucleotide primer with a 5'-terminal oligoribonucleotide segment. (FIG. 4). This second oligonucleotide primer hybridizes to the single-stranded RNA, and the DNA polymerase uses the single-stranded RNA as a template to synthesize a complementary DNA by extending the second oligonucleotide primer, thereby forming an RNA-DNA hybrid. The ribonuclease hydrolyzes the RNA which is part of the RNA-DNA hybrid to liberate the complementary DNA comprising the second oligonucleotide primer at its 5' terminus. The first oligonucleotide primer hybridizes to the complementary DNA and the DNA polymerase uses the complementary DNA as template to synthesize a DNA second template by extending the first oligonucleotide primer. The ribonuclease hydrolyzes the RNA portion of the second oligonucleotide primer, which together with the second DNA template comprises an RNA-DNA hybrid. This allows the 3'-terminal DNA sequence to hybridize to the plus-sense sequence of the initiation site in the DNA second template. Then the DNA polymerase uses the DNA second template to synthesize the promoter by extending the DNA second template. Finally, an RNA polymerase recognizes the promoter and transcribes the DNA second template, thereby providing copies of the RNA first template. (FIG. 4).

An RNA first template may be provided by adding to the reaction a single-stranded complementary DNA comprising a sequence complementary to the specific nucleic acid sequence and a 5'-terminal second oligonucleotide primer with a oligoribonucleotide segment. The single-stranded complementary DNA may be generated in a separate process as set forth in the preferred mode starting from a single-stranded DNA comprising a specific nucleic acid sequence, in this case using a second oligonucleotide primer comprising a 5'-terminal oligoribonucleotide segment. The complementary DNA is used to provide an RNA first template as set forth in the alternative mode starting from a single-stranded RNA comprising a specific nucleic acid sequence.

All of the enzymes used in this invention should meet certain practical specifications. Each enzyme or enzyme preparation should be free of deleterious deoxyribonuclease ("DNase") activities, such as the 5' or 3' exonuclease activities which are often associated with certain DNA polymerases and single-strand or double-strand specific exonuclease or endonucleases. Each enzyme or enzyme preparation should be free of deleterious ribonuclease ("RNase") activities, with the exception of the preferred addition of a ribonuclease activity which is specific for hybrids of an RNA and DNA (for example, ribonuclease H). In addition, each enzyme should be reasonably active under the common reaction conditions which are used for the other enzymatic processes, and non-enzymatic processes, such as hybridizing oligonucleotide primers to the RNA or DNA templates.

The RNA polymerase which is used in this invention may be any enzyme capable of binding to a particular DNA sequence called a promoter and specifically initiating an RNA synthesis at a defined initiation site within close proximity to the promoter. Sequences of the promoter and the initiation site form part of the RNA first template and the DNA second template, and may be provided as part of the second primer. The RNA polymerase should be capable of synthesizing several copies of an RNA per functional copy of template in a reasonable amount of time. In addition, the RNA polymerase should recognize a relatively compact promoter and initiation site, a feature that characterizes a family of bacteriophage RNA polymerases. In the preferred embodiment, the bacteriophage T7 RNA polymerase is used. In another embodiment, the bacteriophage T3 RNA polymerase is used. In addition, other bacteriophage RNA polymerases, such as Salmonella phage sp6, Phage K11 or phage BA14 may be used. Alternatively, another prokaryotic or a eukaryotican RNA polymerase may be used. It is recognized that if alternative RNA polymerases are used, then the necessary changes to the promoter and initiation sequences of the second primer should be made according to the template specificity of the particular RNA polymerase.

The DNA polymerase which is used in this invention may be any enzyme capable of synthesizing DNA from an oligonucleotide primer and a DNA or an RNA template. In addition, this enzyme may contain an RNase H activity. In the preferred embodiment, the avian myeloblastosis viral polymerase ("AMV reverse transcriptase") is used. In addition, the DNA polymerase could be from another retrovirus, such as Moloney murine leukaemia virus. Alternatively, any other eukaryotic, prokaryotic or virus encoded a DNA polymerases could be used.

The RNase H which could be used in this invention may be any enzyme capable of hydrolyzing an RNA which is annealed to a complementary DNA. This enzyme should not be capable of hydrolyzing single-or double-stranded RNA or DNA. In the preferred embodiment, the E. coli RNase H is used. In addition, other RNase H enzymes could be used, such as calf thymus RNase H. Since RNase H is an intrinsic activity of AMV reverse transcriptase, the E. coli RNase H will be supplemented in the preferred embodiment by the RNase H of AMV reverse transcriptase. Alternatively, any other enzyme capable of separating an RNA from DNA could be used.

The above-mentioned enzymes and primers are mixed together in a reaction vessel which contains the necessary buffers and co-factors for both DNA and an RNA synthesis. In addition, the ionic conditions and reaction temperature should be compatible with specific hybridization of the primers to the DNA and an RNA templates as is known to those skilled in the art. The reaction mixture should be free of such agents which would interfere with the amplification process, specifically substances which could greatly inhibit the activity of the enzymes, interfere with the hybridizing of primers and templates, or degrade non-productively the nucleic acid intermediates and products.

As described in U.S. Pat. No. 5,130,238, the addition of both DMSO and BSA to the reaction medium significantly increases the sensitivity and reproducibility of the above-described amplification process. DMSO at final concentrations in the range between 0% and 30% and BSA at final concentrations in the range between 0.5 µg/ml to 2500 µg/ml are useful for enhancing the sensitivity and reproducibility of the amplification process.

The use of DMSO and BSA in the amplification reaction medium provides enhanced sensitivity and reproducibility over the use of the reaction medium without DMSO and BSA, however the reaction medium alone is sufficient for the detection and isolation of targeted nucleic acid sequences.

EXAMPLE 1

Design and Synthesis of Oligonucleotide Primers and an RNA Template for TRAM

Enzymes for digesting and ligating DNA were purchased from New England Biolabs, and used according to the supplier's recommendations. E. coli strain HB101 (ATCC 33694) was used for all transformations. E. coli transformants were grown on YT medium (Miller, 1972) containing 50 µg/ml ampicillin. Plasmid DNA was purified by a rapid boiling method (Holmes and Quigley, 1981). DNA fragments and vectors used for all constructions were separated by electrophoresis on low melting point agarose, and purified from the molten agarose by phenol extraction and ethanol precipitation (Maniatis et at., 1982). Plasmid DNA was sequenced using a modification (Hattori et at., 1985) of the dideoxy method (Sanger et al., 1977). Reactions were run using the −20 universal primer (New England Biolabs). A plasmid, pGEM3X-HIV1, was constructed for the transcription of model RNA templates, by subcloning a 1.5-kb proviral DNA fragment of HIV HXB2 (Genbank Accession Number K03455) into a derivative of pGEM 3 (Promega). Another DNA fragment of HIV HXB2 was excised using Sau3AI site at nucleotide 1015 and the Pvu II site at nucleotide 1144, and was ligated into pGEM3X-HIV1 using the Pst I site at nucleotide 1414 and the Sph I site at nucleotide 1442, and the synthetic adapter GATCTGCA (to join the Sau3AI and Psi I ends) and the Sph I linker CGCATGCG (to convert the Pvu II and to an Sph I end). The resulting plasmid, pGEM3X-HIV1-E2 was used for the transcription of RNA templates as follows: approximately 1 µg of pGEM3X-HIV1-E2 was digested with Eco RI, precipitate with ethanol, dissolved in 5 µl of water, and added to a 20-µl (final volume) reaction containing 40 mM Tris-HCl (pH 8.5), 12 mM MgCl$_2$, 50 mM KCl, 10 mM dithiotheitol, 2 mM ATP, 2 mM CTP, 2 mM GTP, 2 mM UTP, 1 mM dATP, 1 mM dCTP, 1 mM dGTP, 1 mM dTTP, 12.5 units RNA-Guard (Pharmacia) and 30 units SP6 an RNA polymerase (Promega). The transcription reaction was incubated at 37° C. for 1 hour; thereafter 1 µl (1 unit) of RQ DNase I (Promega) was added, and the incubation was continued for an additional 15 min. The resulting RNA product, HIV1-E2 RNA, was then extracted twice with phenol:chloroform (1:1) and once with chloroform, precipitated with ethanol, and dissolved in water. The concentration of HIV1-E2 RNA was determined by slot-blot hybridization by comparing serial dilutions of the RNA to known amounts of the plasmid DNA. The specific nucleic acid (RNA) sequence and its complementary DNA sequence, which hybridize to the respective second primer and first primer are disclosed in FIG. 5 (SEQ.ID. No. 2 and 3).

A TRAM second primer was synthesized as a 78-base oligodeoxynucleotide with a chemically-coupled 5'-terminal phosphate (FIG. 6A, SEQ. ID. No. 4). It comprises a 34-base 5'-terminal sequence, capable of folding into a 10-base loop flanked by a 12-base pair duplex, which further comprises a T7 RNA polymerase initiation site; a 22-base internal sequence comprising the minus-sense sequence of a T7 RNA polymerase promoter; and a 22-base 3'-terminal priming sequence which anneals to the specific nucleic acid sequence of the analyte (nucleotides 113–134 of SEQ. ID. No. 2; complement to nucleotides 1497–1518 of Genbank Accession Number K03455). As a control, a dephosphorylated TRAM second primer was synthesized as shown in FIG. 6A but without a chemically-coupled 5'-terminal phosphate. For comparison, a NASBA™ second primer was synthesized as a 48-base oligodeoxynucleotide (FIG. 6B, SEQ.ID. No. 5). It comprises a 26-base 5'-terminal sequence comprising the plus-sense sequence of a T7 RNA polymerase promoter and initiation site; and a 22-base 3'-terminal priming sequence which anneals to the same specific nucleic acid sequence of the analyte as the TRAM second primer. A common first primer was synthesized as a 21-base oligodeoxynucleotide (FIG. 6C, SEQ. ID. No. 6). It comprises a sequence that anneals to a DNA complementary to the specific nucleic acid sequence of the analyte (nucleotides 1–21 of SEQ. ID. No. 2; nucleotides 1091–1111 of Genbank Accession Number K03455). Oligonucleotides were synthesized using an Applied Biosystems 380A DNA synthesizer. Columns, phosphoramidites, and reagents used for oligonucleotide synthesis were obtained from Applied Biosystems, Inc. through Technical Marketing Associates. Oligonucleotides were purified by polyacrylamide gel electrophoresis followed by DEAE cellulose chromatography. Alternatively, purified oligonucleotides were purchased from Synthetic Genetics (San Diego, Calif., USA).

EXAMPLE 2

The Effect of 5'-Phosphorylated Second Primer and DNA Ligase on the Efficiency of Specific Amplification Each standard reaction contained 40 mM Tris-HCl (pH 8.5), 12 mM MgCl$_2$, 50 mM KCl, 10 mM dithiothreitol, 2 mM ATP, 2 mM CTP, 2 mM GTP, 2 mM UTP, 1 mM dATP, 1 mM dCTP, 1 mM dGTP, 1 mM dTTP, 15% (v/v) dimethyl sulfoxide, 100 µg/ml bovine serum albumin, 8 units AMV reverse transcriptase (Seikagaku), 0.1–0.2 units E. coil RNase H (Pharmacia), 20–40 units T7 an RNA polymerase (Pharmacia) and 12.5 units RNA-Guard™ (Pharmacia) in a final volume of 25 µl. In addition, some of the standard reactions contained 2 nM phosphorylated TRAM second primer and 2 nM first primer; of these one control set (Set C) contained no ligase, and other sets (Sets D and E) contained T4 DNA ligase from either New England Biolabs (400 units) or Bethesda Research Laboratories (1 unit), respectively. In addition, one control set (Set B) of standard reactions contained 2 nM dephosphorylated TRAM second primer and 2 nM first primer. In addition, one control set (Set A) of standard reactions (designated as "standard NASBA™ reactions") contained 200 nM NASBA™ second primer and 200 nM first primer. Duplicate reactions from each set of conditions contained 10$^4$ molecules of an RNA template, which was generated following the teaching of Example 1. One reaction from each set of conditions contained no added template. The reactions were incubated at 40° C. for 90 minutes.

Aliquots (5 μl) of the reactions were analyzed by electrophoresis on gels composed of 3% Nusieve agarose, 1% agarose and 0.2 μg/ml ethidium bromide in 1×TAE (40 mM Tris-acetate, 1 mM disodium EDTA, pH 8.0), using a running buffer of 1 x TALE. The separated nucleic acid products were visualized on an ultra-violet transilluminator. Following electrophoresis, the nucleic acids were electroblotted onto a nylon membrane (Hybond ND) using the model TE 42 transfer apparatus as specified by the manufacturer (Hoeffer Scientific Instruments). The transfer was performed in 1×TAE buffer for 1 hour at 600 mA or for overnight at 20 mA. After allowing the membrane to dry, the nucleic acids were fixed by irradiation at 300 nm for 2 minutes on a UV transilluminator.

The membrane was next hybridized with a [5'-$^{32}$P] oligonucleotide probe (5'-CCAGGCCAGATGAGAGAACCAAGGGGAAG-3') (SEQ. ID. NO.7). The labelled probe was added at a concentration of 1×10$^6$ cpm per ml of hybridization solution, which contained 0.9M NaCl, 0.09M sodium citrate, 0.1% bovine serum albumin, 0.1% polyvinylpyrilidone (40000), 0.1% Ficoll (400000), 25 mM Tris-HCl (pH 7.5), 0.05 % sodium pyrophosphate and 0.5% sodium dodecyl sulfate. Hybridization was performed for a minimum of 2 hours at 50° C. After hybridization, the membrane was washed in a solution containing 15 mM NaCl, 1.5 mM sodium citrate and 0.5% sodium dodecyl sulfate first for 5 minutes at room temperature and then for 30 minutes at 50° C. The membrane was rinsed once in a similar solution, air dried and covered in a plastic wrap. Autoradiography was performed using Kodak XAR-5 fill with intensifying screens at -70° C. for required exposures.

The blot hybridization analysis of the reaction products (FIG. 7) shows that the most specific amplification was observed for reactions containing both phosphorylated TRAM second primer and DNA ligase (Sets D and E, lanes 2 and 3). The absence of DNA ligase in the reaction results in a substantial loss in the amount of specific product, which migrates differently on the native agarose gel (Set C, lanes 2 and 3). For reactions containing the dephosphorylated TRAM second primer and no DNA ligase, the specific products were only marginally detected by hybridization (Set B, lanes 2 and 3). The accumulation of specific products in the reactions of Sets D or E was comparable to that in reactions containing the NASBA™ second primer (Set A, lanes 2 and 3). For each set of conditions, specific products were not detected from reactions without added template (Sets A through E, lanes 1).

Figure 7:
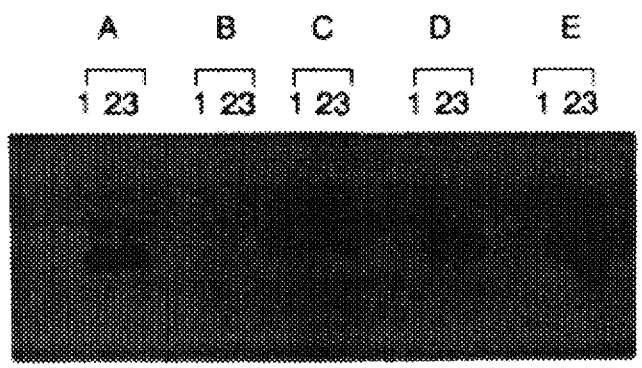
FIG. 7 shows the effect of 5'-phosphorylated second primer and DNA ligase on the efficiency of specific amplification in TRAM.

In FIG. 7, the following lanes contain the following materials,

1—no added template
2,3—10$^4$ molecules of HIV-1 E2 RNA as template
A—NASBA™
B—TRAM reactions containing dephosphorylated second primer
C—TRAM reactions containing phosphorylated second primer
D—TRAM reactions containing phosphorylated second primer+ligase (400 U, NEB)
E—TRAM reactions containing phosphorylated second primer+ligase (1 U, BRL)

EXAMPLE 3

The Effect of 5'-Phosphorylated Second Primer and DNA Ligase on the Structures of Amplified RNA Products Standard reactions were assembled following the teaching of Example 2. In addition, two sets of standard reactions contained 500 fmol (20 nM) first primer, 50 fmol (2 nM) dephosphorylated TRAM second primer, and either no ligase (Set A) or 1 unit T4 DNA Ligase from BRL (Set B). In addition, two sets of standard reactions contained 500 fmol (20 nM) first primer, 50 fmol (2 nM) phosphorylated TRAM second primer, and either no ligase (Set C) or 1 unit of T4 DNA Ligase from BRL (Set D) . In addition, one control set (Set N) of standard reactions contained 200 nM NASBA™ second primer and 200 nM first primer. Reactions from each set of conditions contained 10$^6$ molecules of an RNA template, which was generated following the teaching of Example 1. The reactions were incubated at 40° C. for 90 minutes.

The RNA products of each reaction were analyzed by direct dideoxy sequencing using the first primer. Aliquots (5 to 10 μl) of the reactions were purified by centrifugal desalting using columns consisting of micropipet tips plugged with glass wool and packed with 500 μl of Bio-gel P60 (Bio-Rad) in 40 mM Tris-HCl (pH 7.2) and 50 mM NaCl. The eluents from the columns (5-μl) containing the amplified RNA products were added to a 5-μl mixture containing 80 mM Tris-HCl (pH 8.3), 100 mM KCl, 12 mM MgCl$_2$10 mM dithiothreitol and 0.5 pmol [5'-$^{32}$P] first primer. The resulting priming mixture was incubated at 50 to 60° C. for 5 minutes and then cooled to room temperature over a time interval of 5 minutes. After adding 1 μl (10 to 15 units) of AMV reverse transcriptase, the annealed priming mixture was divided into 2.2-μl aliquots and added to four tubes each containing 2 μl of a different dNTP/ddNTP mixture. The resulting dideoxy sequencing reactions were incubated at 48° C. for 15 minutes. To each reaction was then added 2 μl of a chase solution (0.5 mM of each dNTP), and the incubation at 48° C. was continued for an additional 10 minutes. To each completed sequencing reaction was then added 4 μl of sequencing dye mixture (95% fomamide, 20 mM EDTA, 0.05% bromophenol blue and 0.05% xylene cyanol FF) and 1 μl (1 unit) RNase A. Following a 15-minute incubation at 37° C. to digest the excess RNA, the labelled DNA sequencing products were boiled for 2 minutes and quick-cooled on ice. Aliquots (2 to 2.5 μl) of each sample were applied to a standard 7% polyacrylamide sequencing gel and analyzed using standard electrophoretic methods. Autoradiography was performed using Kodak XAR-5 film for required exposures.

Figure 8:
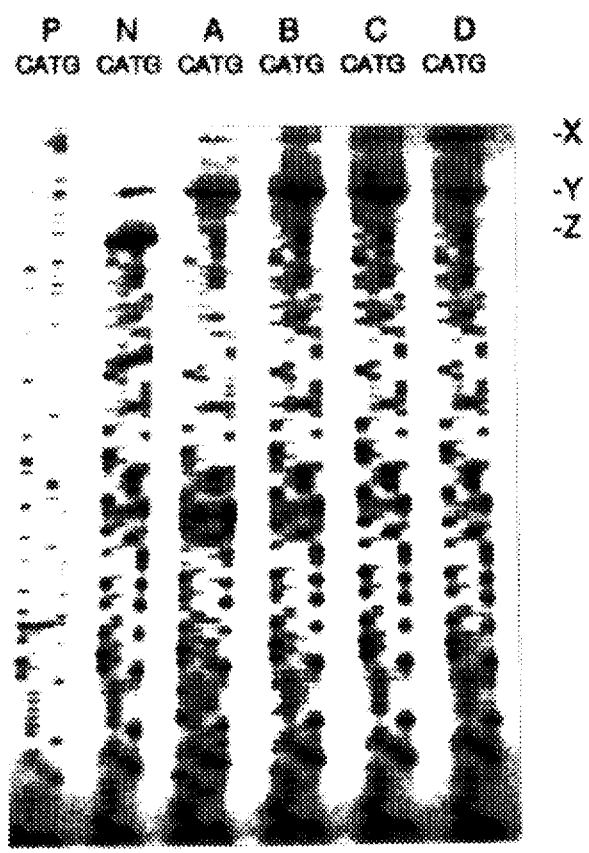
FIG. 8 shows the effect of 5'-phosphorylated second primer and DNA ligase on the structures of amplified RNAs as determined by nucleotide sequence analysis.

Sequencing analysis of the amplified RNA products is shown in FIG. 8.

In FIG. 8, the following lanes contain the following materials, P1 P—Sequence of plasmid DNA of amplified region N—Sequence of NASBA™ RNA product
A—Sequence of TRAM RNA product amplified using the dephosphorylated second primer
B—Sequence of TRAM RNA product amplified using the dephosphorylated second primer+ligase
C—Sequence of TRAM RNA product amplified using the phosphorylated second primer
D—Second of TRAM RNA product amplified using the phosphorylated second primer +ligase Although the amplified RNA products each contained the specific nucleic acid sequence of the added template, variations in the 5'-terminal structures were observed among the different reactions. The reaction containing both phosphorylated TRAM second primer and DNA ligase (Set D) gave predominantly the anticipated RNA product, indicated by extension product X in FIG. 8. The sequencing analysis of this RNA product suggests a 5'-terminal stem-loop structure with a sequence complementary to the 5'-terminal 34 bases of the TRAM second primer (FIG. 6A). As indicated by the shorter extension product Y in FIG. 8, this stem-loop structure was predominantly absent from the amplified RNA products from the reactions with a dephosphorylated TRAM second primer (Sets A and B) or without a DNA ligase (Sets A and C). These shorter RNA products still contained the plus-sense sequence of the T7 promoter, which were absent from the RNA products of a standard NASBA™ reaction (Set N) as indicated by extension product Z in FIG. 8. Thus, the phosphorylated TRAM second primer and DNA ligase are both required for the efficient formation of a DNA intermediate which is capable of amplification without a cyclic use of TRAM second primer.

EXAMPLE 4

The Effect of First Primer Concentration in TRAM

Standard reactions were assembled following the teaching of Example 2. In addition, three sets of standard reactions contained 1 unit T4 DNA ligase (BRL) and 50 fmol (2 nM) phosphorylated TRAM second primer; and first primer in amounts (final concentrations) of 5 pmol (200 nM) for Set B, 500 fmol (20 nM) for Set C, or 50 fmol (2 nM) for Set C. In addition, a control set (Set A) of standard reactions contained 5 pmol (200 nM) NASBA™ second primer and 5 pmol (200 nM) first primer. Duplicate reactions from each set of conditions contained $10^6$, $10^4$, $10^2$ molecules of an RNA template, which was generated following the teaching of Example 1. One reaction from each set of conditions contained no added template. The reactions were incubated at 40° C. for 90 minutes.

Aliquots (5 μl) of the reactions were analyzed by agarose gel electrophoresis and blot hybridization following the teaching of Example 2. Visualization of the ethidium bromide stained products (FIG. 9) shows that the levels of accumulated products depend on the amount of the first primer in the reaction.

The concentration of the first primer also affects the relative accumulation of RNA and RNA:DNA hybrid products, indicated by X and Y respectively. The RNA:DNA hybrid, which was abundant in reactions containing 5 pmol (20 nM) first primer (Set B), virtually disappeared in reactions containing 500 fmol (20 nM first primer (Set C). Although the levels of RNA product were unaffected at either of these first primer concentrations, a further decrease in the first primer concentration to 2 nM (Set D) resulted in a proportional decrease in the level of accumulated RNA product.

Some of the reactions (e.g., Set B, lanes 1, 4, 5, 6 and 7; and Set C, lanes 1, 6 and 7) contained other products which were smaller than the RNA product and did not hybridize to the oligonucleotide probe. These non-specific products were predominant in reactions containing higher concentrations of first primer or lower levels of added template. For example, in the reactions containing $10^4$ molecules of added template (lanes 4 and 5), the non-specific products prevailed at first primer concentrations of 200 nM (Set B) but not at 20 mM (Set C). Similarly, the same high first primer concentration (200 nM) in reactions containing the NASBA™ second primer (Set A) resulted in the predominance of non-specific products with added template levels of $10^4$ molecules or less (lanes 1, 4, 5, 6 and 7). Thus for both TRAM and NASBA™ second primers, there was more non-specific primer interaction at the higher first primer concentrations.

Figure 10:
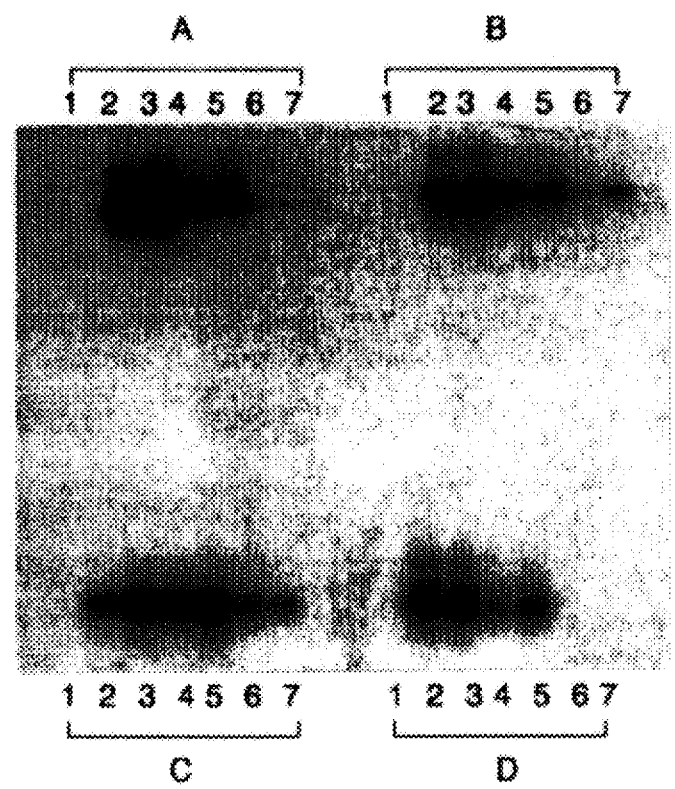

The competition between non-specific and specific products was also evident from the blot hybridization analysis (FIG. 10).

Figure 9:
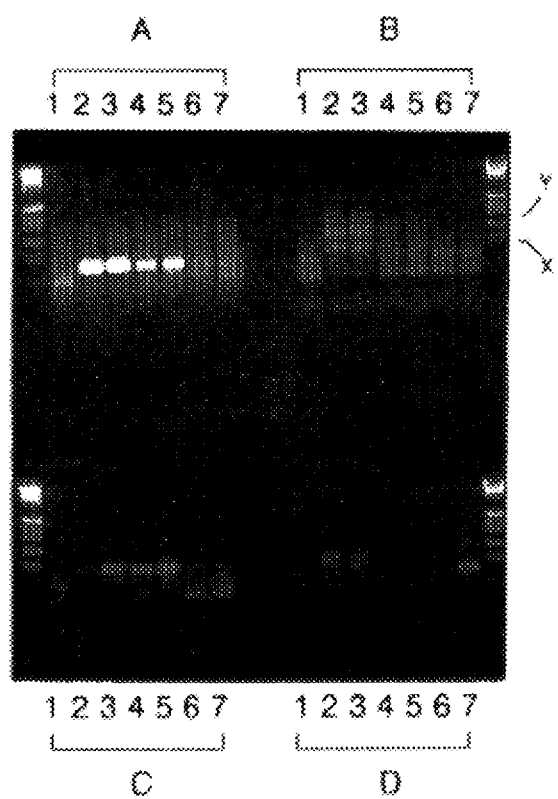
FIGS. 9 and 10 show the effect of first primer concentration in TRAM.

In FIGS. 9 and 10, the following lanes contain the following materials,

1—no added template
2,3—$10^6$ molecules of HIV-1 E2 RNA as template
4,5—$10^4$ molecules of HIV-1 E2 RNA as template
6,7—$10^2$ molecules of HIV-1 E2 RNA as template
A—NASBA™ (second primer=5 pmol; first primer=5 pmol)
B—TRAM (second primer=50 fmol; first primer=5 pmol)
C—TRAM (second primer=50 fmol; first primer=500 fmol)
D—TRAM (second primer=50 fmol; first primer=50 fmol)

For both NASBA™ (Set A) and TRAM (Set B) second primers, in reactions containing 5 pmol (200 nM) first primer, $10^2$ molecules of added template were only marginally amplified and/or detected. However, the $10^2$ molecules of added template were more reliably amplified and/or detected in reactions containing the TRAM second primer and 500 fmol (20 nM) first primer (Set C). A further decrease in the level of first primer to 50 fmol (2 nM), resulted in a loss of product yield and sensitivity (Set D). Thus, in reaction containing 50 fmol (2 nM) TRAM second primer, the optimum specific amplification was obtained with 500 fmol first primer per reaction (20 nM).

EXAMPLE 5

The Effect of Second Primer Concentration in TRAM

Standard reactions were assembled following the teaching of Example 2. In addition, three sets of standard reactions contained 1 unit T4 DNA ligase (BRL) and 500 fmol (20 nM) first primer; and phosphorylated TRAM second primer in amounts (final concentrations) of 50 fmol (2 nM) for Set B, 5 fmol (0.2 nM) for Set C, or 0.5 fmol (0.02 nM) for Set C. In addition, a control set (Set A) of standard reactions contained 5 pmol (200 nM) NASBA™ second primer and 5 pmol (200 nM) first primer. Duplicate reactions from each set of conditions contained $10^6$, $10^4$, or $10^2$ molecules of an RNA template, which was generated following the teaching of Example 1. One reaction from each set of conditions contained no added template. The reactions were incubated at 40° C. for 90 minutes.

Aliquots (5 μl) of the reactions were analyzed by agarose gel electrophoresis and blot hybridization following the teaching of Example 2. Visualization of the ethidium bromide stained products (FIG. 11) and autoradiography of the specifically hybridized products (FIG. 12) indicate that, the levels of accumulated products were less dependent on the amount of second primer in the reaction.

Figure 11:
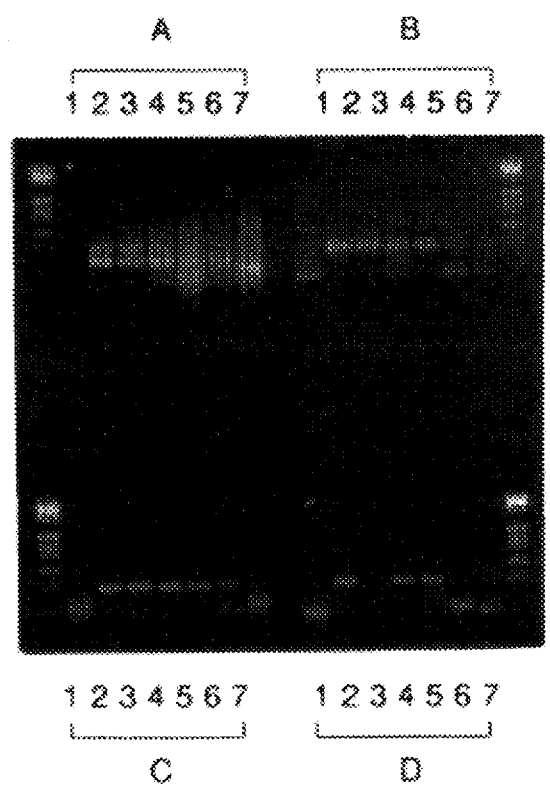
FIGS. 11 and 12 show the effect of second primer concentration in TRAM.
Figure 12:
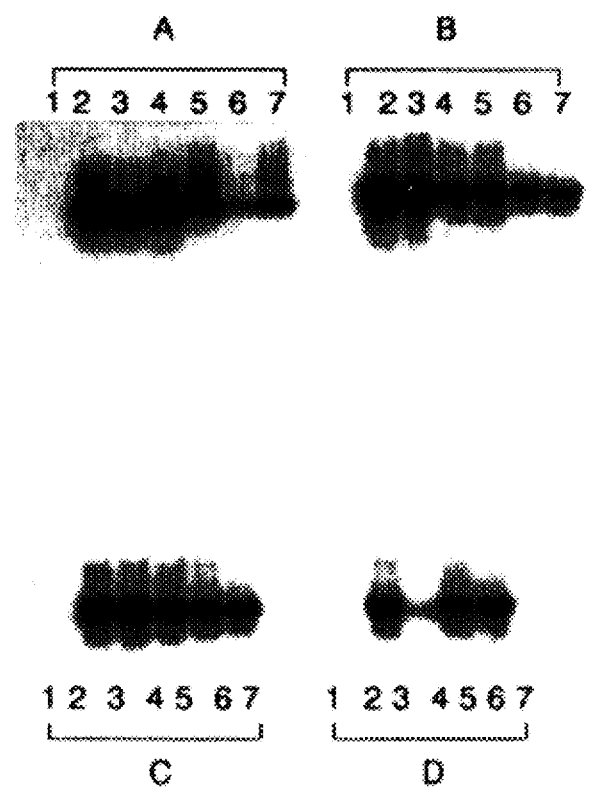

In FIGS. 11 and 12, the following lanes contain the following materials,

1—no added template
2,3—$10^6$ molecules of HIV-1 E2 RNA as template
4,5—$10^4$ molecules of HIV-1 E2 RNA as template
6,7—$10^2$ molecules of HIV-1 E2 RNA as template
A—NASBA™ (second primer=5 pmol; first primer=5 pmol)
B—TRAM (second primer=50 fmol; first primer=500 fmol)

C—TRAM (second primer=5 fmol; first primer=500 fmol)

D—TRAM (second primer=0.5 fmol; first primer=500 fmol)

The most specific product was observed in reactions containing 50 fmol (2 nM) TRAM second primer (Set B). Lowering the level of TRAM second primer to 5 fmol (0.2 nM) caused only a slight reduction in the yield of specific products and sensitivity at $10^2$ molecules of added template (Set C). However, both product yield and sensitivity were adversely affected in the reactions containing 0.5 fmol (0.02 nM) TRAM second primer (Set C). The sensitivity of amplification and/or detection down to 102 molecules of added template was similar in reactions containing either 5 pmol (200 nM) NASBA™ second primer (Set A) or 50 fmol (2 nM) TRAM second primer (Set B). Thus, 50 fmol TRAM second primer per reaction (2 nM) was optimum, in conjunction with the optimum of 500 fmol (20 nM) first primer.

EXAMPLE 6

The Effect of First Comparison of TRAM with NASBA™ Using the Primer Concentrations Optimized for TRAM also for NASBA™

Standard reactions were assembled following the teaching of Example 2. In addition, one set (Set B) of standard reactions (designated as "optimized TRAM reactions") contained 1 unit T4 DNA ligase (BRL) and 50 fmol (2 nM) phosphorylated TRAM second primer and 500 fmol (20 nM) first primer in amounts. In addition, another set (Set A) of standard reactions contained 50 fmol (2 nM) NASBA™ second primer and 500 fmol (20 nM) first primer. Duplicate reactions from each set of conditions contained $10^6$, $10^4$, or $10^2$ molecules of an RNA template, which was generated following the teaching of Example 1. One reaction from each set of conditions contained no added template. The reactions were incubated at 40° C. for 90 minutes.

Aliquots (5 µl) of the reactions were analyzed by agarose gel electrophoresis and blot hybridization following the teaching of Example 2. Visualization of the ethidium bromide stained products (FIG. 13) and autoradiography of the specifically hybridized products (FIG. 14) indicates that no products were detected at any level of added template from NASBA reactions containing 50 fmol (20 nM) first primer.

Figure 13:
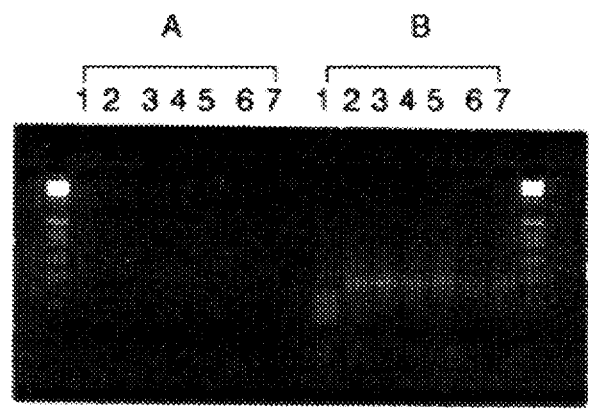
FIGS. 13 and 14 show the effect of first comparison of TRAM with NASBA™ using the primer concentrations optimized for TRAM also for NASBA™.
Figure 14:
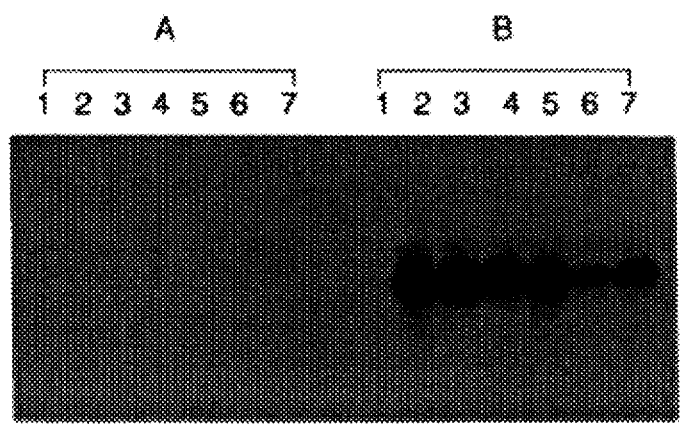

In FIGS. 13 and 14, the following lanes contain the following materials,

1—no added template
2,3—$10^6$ molecules of HIV-1 E2 RNA
4,5—$10^4$ molecules of HIV-1 E2 RNA
6,7—$10^2$ molecules of HIV-1 E2 RNA
A—NASBA™ (second primer=50 fmol; first primer=500 fmol)
B—TRAM (second primer=50 fmol; first primer=500 fmol)

Conversely, these same primer concentrations in the optimized TRAM reactions resulted in the amplification and detection of specific product down to $10^2$ molecules of added template. These results demonstrate a major difference in the NASBA™ and TRAM processes showing the effect of the specialized structure of the second primer for TRAM (cf FIG. 6A with 6B).

EXAMPLE 7

Second Primer Independence for Re-amplification of TRAM Reaction Products

Standard NASBA™ reactions and optimized TRAM reactions were assembled following the teachings of Examples 2 and 6, respectively. Each reaction contained $10^4$ molecules of an RNA template, which was generated following the teachings of Example 1. The reactions were incubated at 40° C. for 90 minutes. A portion of each incubated reaction was treated with DNase I to remove any residual primers. Serial 10-fold dilutions to $10^{-14}$ were prepared for both DNase I treated and untreated portions of both NASBA™ and TRAM reactions.

Standard reactions were assembled following the teaching of Example 2. In addition, the standard reactions contained first primer in amounts (final concentrations) of 5 pmol (200 nM) for Set A, and 500 fmol (20 nM) for Set B. Duplicate reactions from Set A contained 2-µl aliquots of the $10^{-11}$, $10^{-12}$, $10^{-13}$ or $10^{-14}$ dilutions of the DNase I treated or untreated portions of the standard NASBA™ reactions. Duplicate reactions from Set B contained 2-µl aliquots of the $10^{-9}$, $10^{-10}$, $10^{-11}$, $10^{-12}$ dilutions of the DNase I treated or untreated portions of the optimized TRAM reactions. One reaction from each set of conditions contained no added template. The reactions were incubated at 40° C. for 90 minutes.

Aliquots (5 µl) of the reactions were analyzed by agarose gel electrophoresis and blot hybridization following the teaching of Example 2. Visualization of the ethidium bromide stained products (FIG. 5) and autoradiography of the specifically hybridized products (FIG. 16) indicates that, the serially-diluted and untreated TRAM products could be amplified in standard reactions containing the first primer only.

Figure 15:
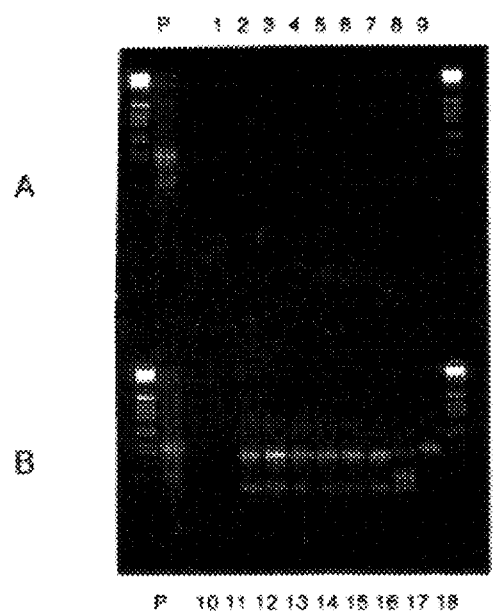
FIGS. 15 and 16 show second primer independence for re-amplification of TRAM reaction products.
Figure 16:
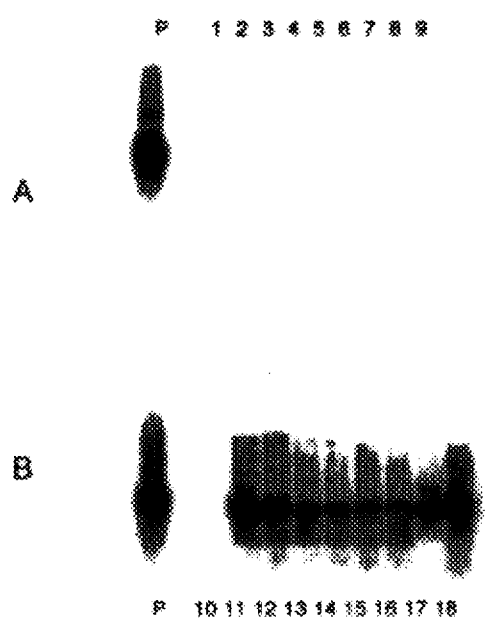

In FIGS. 15 and 16, the following lanes contain the following materials,

1—no added template
2,3—2 µl of $10^{-11}$ dilution of a NASBA™ reaction as template
4,5—2 µl of $10^{-12}$ dilution of a NASBA™ reaction as template
6,7—2 µl of $10^{-13}$ dilution of a NASBA™ reaction as template
8,9—2 µl of $10^{-14}$ dilution of a NASBA™ reaction as template
10—no added template
11,12—2 µl of $10^{-9}$ dilution of a TRAM reaction as template
13,14—2 µl of $10^{-10}$ dilution of a TRAM reaction as template
15,16—2 µl of $10^{-11}$ dilution of a TRAM reaction as template
17,18—2 µl of $10^{-12}$ dilution of a TRAM reaction as template
A—NASBA™ reactions containing 5 pmol of first primer and no second primer
B—TRAM reactions containing 500 fmol of first primer and no second primer
P—Positive hybridization control Specific products were amplified and detected from products of optimized TRAM reactions that had been diluted to $10^{-11}$ (FIG. 14, Set B, lanes 15 and 16) or $10^{-12}$ (FIG. 15, Set B, lanes 17 and 18). Conversely, the untreated products of the standard NASBA™ reaction, at any dilution, could not be amplified without the NASBA™ second primer (Set A, lanes 2 through 9). Similar results were obtained using serial dilutions of the DNase I treated NASBA™ and TRAM reactions (data not shown).

The RNA product of a NASBA™ reaction does not carry a promoter sequence from which a double-stranded DNA promoter may be synthesized. Rather, the promoter sequence is carried in the second primer which must be used as a template in each cycle to restore a functional double-stranded promoter to the DNA product of the RNA template. However, the unique arrangement of the promoter relative to the terminal stem-loop in the TRAM DNA product provides for the transcription of a TRAM RNA product, that carries a minus-sense sequence of the promoter. Using the TRAM RNA product as template, a DNA product with a double-stranded promoter can be synthesized without requiring a promoter-containing primer at each cycle. Thus, the phosphorylated TRAM second primer and DNA ligase are required for initiation of amplification to form the initial DNA products from the added template, but not for cyclic propagation of amplification from the RNA and DNA products of a TRAM reaction.

EXAMPLE 8

First Primer Dependence for Re-amplification of TRAM Reaction Products

Standard reactions were assembled following the teaching of Example 2. In addition, one set (Set B) of standard reactions contained 500 fmol (20 nM) first primer. Another set (Set A) of standard reactions contained no additional primers. Duplicate reactions from each set of conditions contained 2-µl aliquots of the $10^{-9}$, $10^{-10}$, $10^{-11}$, $10^{-12}$ dilutions of the optimized TRAM reactions, which were generated following the teaching of Example 7. One reaction from each set of conditions contained no added template. The reactions were incubated at 40° C. for 90 minutes.

Aliquots (5 µl) of the reactions were analyzed by agarose gel electrophoresis and blot hybridization following the teaching of Example 2. Visualization of the ethidium bromide stained products (FIG. 17) and autoradiography of the specifically hybridized products (FIG. 18) indicates that, the serially-diluted TRAM products could not be amplified in standard reactions without primers (Set A, lanes 2 through 7).

Figure 17:
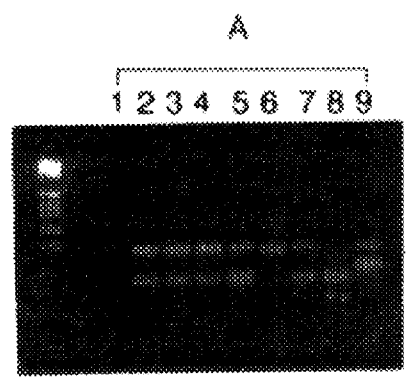
FIGS. 17 and 18 show first primer dependence for re-amplification of TRAM reaction products.
Figure 18:
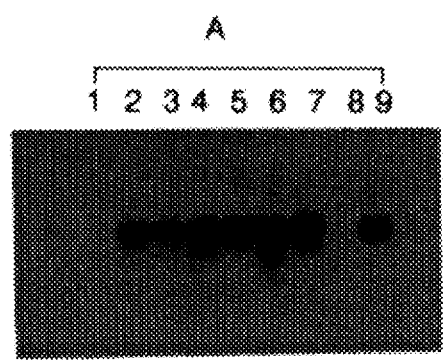

In FIGS. 17 and 18, the following lanes contain the following materials,

1—no added template 2,3—2 µl of $10^{-9}$ dilution of DNase 1 treated TRAM products 4,5—2 µl of $10^{-10}$ dilution of DNase 1 treated TRAM products 6,7—2 µl of $10^{-11}$ dilution of DNase 1 treated TRAM products 8,9—2 µl of $10^{-12}$ dilution of DNase 1 treated TRAM products A—TRAM reactions containing 500 fmol first primer only However, as was shown in Example 8, dilutions of a TRAM reaction down to $10^{-12}$ were effectively amplified in standard reactions containing only the first primer (Set B, lanes 2 through 7). Thus, the first primer is required for the cyclic propagation of amplification from the RNA and DNA products of a TRAM reaction.

EXAMPLE 9

Effect of ITP on TRAM Reactions

Standard NASBA™ reactions and optimized TRAM reactions were assembled following the teachings of Examples 2 and 6, respectively. In addition, one set of standard NASBA™ reactions and optimized TRAM reactions were assembled with a mixture of 1 mM GTP and 1 mM ITP replacing the standard 2 mM GTP. Each reaction contained 40 µCi [$\propto-^{32}$P]CTP (3000 Ci/mmol), which was supplied by New England Nuclear (Cambridge Mass.), and $10^4$ molecules of an RNA template, which was generated following the teachings of Example 1. The reactions were incubated at 40° C. for 90 minutes.

The levels of total RNA synthesis for each reaction condition were determined by measuring the incorporation of TCA-insoluble radioactivity of each reaction. Aliquots (5 µl) of amplification reactions were quenched in 20 µl 10 mM EDTA and placed on ice until all time point samples had been collected. The quenched samples were then applied to glass filter discs, and immediately dropped into ice-cold 5% trichloroacetic acid ("TCA")—1% sodium pyrophosphate for 10 min with occasional mixing. Two 5 min. washes with ice-cold 5% TCA were followed by two additional washes with 95% ethanol and lyophilization to dryness. Radioactivity was determined in a liquid scintillation counter.

The results, as summarized in Table 1, show the absolute amounts of an RNA synthesized under each reaction condition relative to the amount of an RNA from NASBA™ reactions under standard conditions (2 mM GTP). RNA synthesis from the optimized TRAM reactions without ITP was only 34.5% of that observed from the standard NASBA™ reaction. The substitution of 1 mM ITP for 1 mM GTP had no effect in NASBA™ reactions, but clearly increased the level of total RNA synthesis in TRAM reactions from 34.5% to 84% of that observed in NASBA™. The 5'-terminal stem-loop of a TRAM RNA product is the most ostensible difference from a NASBA™ RNA product, that could explain the relative differences in the enhancement of an RNA synthesis due to ITP. The incorporation of ITP into the RNA product could destabilize the 5'-terminal stem-loop, which would then facilitate its displacement by AMV reverse transcriptase during the synthesis of a DNA copy. This was experimentally shown by P2-primed cDNA synthesis from TRAM RNA products synthesized with or without ITP. Reverse transcriptase paused more readily at the sequence complimentary to the 5'-end of the RNA not containing ITP. Thus, by including 1 mM ITP along with 1 mM GTP in TRAM reactions, the level of transcription was comparable to that of NASBA™.

TABLE 1

| Amplification conditions | % RNA Synthesis 2 mM GTP | % RNA Synthesis 1 mM GTP |
|---|---|---|
| NASBA ™ | 100 | 101 |
| TRAM | 34.5 | 84 |

EXAMPLE 10

The Effect of an RNA-DNA Composite Second Primer on the Structures of Amplified RNA Products A TRAM second primer, as disclosed in FIG. 6A (SEQ. ID. No. 4) and as described in Example 1, was synthesized as a 78-base RNA-DNA composite oligonucleotide comprising a 5'-terminal oligonucleotide segment of 34 ribonucleotides joined via a phosphodiester bond to a 3'-terminal oligonucleotide segment of 44 deoxynucleotides. The 5'-end of the composite TRAM second primer was not phosphorylated.

Standard reactions were assembled following the teaching of Example 2. In addition, two sets of standard reactions contained 500 fmol (20 nM) first primer, 50 fmol (2 nM) phosphorylated TRAM second primer, and either no ligase (Set A) or 1 unit of T4 DNA ligase from BRL (Set B); In addition, a third set of standard reactions contained 500 fmol (20 nM) first primer and 50 fmol (2 nM) composite TRAM second primer. Reactions from each set of conditions contained $10^6$ molecules of an RNA template, which was generated following the teaching of Example 1. The reactions were incubated at 40° C. for 90 minutes.

The RNA products of each reaction were analyzed by direct dideoxy sequencing following the teaching of Example 3. Sequencing analysis of the amplified RNA products is shown in FIG. 19, in comparison with a sequence generated using plasmid DNA from pGEM3X-HIV1 E2 (Set P).

Figure 19:
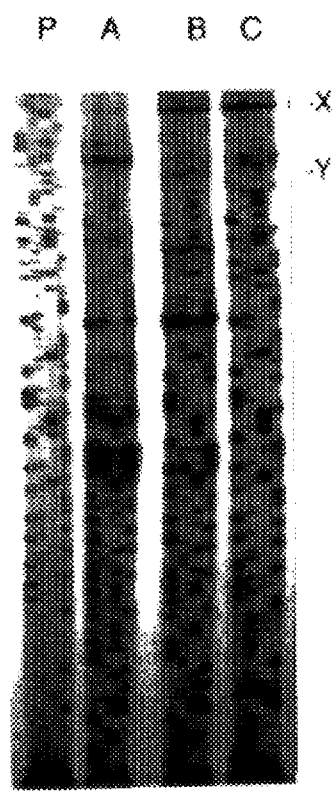
FIG. 19 shows the effect of an RNA-DNA composite second primer on the structures of amplified RNA products as determined by nucleotide sequence analysis.

In FIG. 19, the following lanes contain the following materials,

P—sequence of plasmid DNA in the amplified region

A—sequence of TRAM RNA product amplified using the standard second primer without ligase B—sequence of TRAM RNA product amplified using the standard second primer with ligase C—sequence of TRAM RNA product amplified using the RNA-DNA composite second primer without ligase Although the amplified RNA products each contained the specific nucleic acid sequence of the added template and the plus-sense sequence of the T7 promoter, variations in the 5'-terminal structures were observed among the different reactions. Without DNA ligase, the reaction containing only the phosphorylated TRAM second primer (Set A) gave predominantly the truncated RNA product Y in FIG. 19 (cf. FIG. 8, Set C) that is missing the 5'-terminal stem-loop sequence of the TRAM second primer. The reaction containing both phosphorylated TRAM second primer and DNA ligase (Set B) gave predominantly the anticipated RNA product, indicated by extension product X in FIG. 19 (cf. FIG. 8, Set D). The sequencing analysis of this RNA product suggests a Y-terminal stem-loop structure with a sequence complementary to the 5'-terminal 34 bases of the TRAM second primer (FIG. 6A). The reaction containing the composite TRAM second primer (Set C) gave an RNA product of similar length. Sequence analysis of this RNA product suggests a 5'-terminal stem-loop structure with a sequence identical to the 5'-terminal 34 bases of the composite TRAM second primer (FIG. 6A). The reactions of Sets A and B contain some primer-related non-specific sequences in addition to the specific nucleic acid sequence. The results indicate that the use of a TRAM second primer with a 5'-terminal oligoribonucleotide segment is a viable alternative method for the formation of an RNA product that is capable of amplification without a cyclic use of a TRAM second primer.

EXAMPLE 11

Use of First Primers with 5'-Terminal Stem-Loops for Cyclic Amplification in the Absence of Primers Two alternative first primers were synthesized, each of which comprise a 21-base 3'-terminal priming sequence identical to the first primer (P2) sequence of FIG. 6C and FIG. 20A (SEQ. ID. NO. 8). One of these alternative primers, P2.1, is a 44-base oligodeoxynucleotide (FIG. 20B, SEQ. ID. NO. 9) that further comprises a 23-base 5'-terminal sequence, capable of folding into a 7-base loop flanked by a 8-base pair duplex. The second of these alternative primers, P2.2, is a 30-base oligodeoxynucleotide (FIG. 20C, SEQ. ID. NO. 10) that further comprises a 9-base 5'-terminal sequence capable of folding into a 1-base loop flanked by a 4-base pair duplex.

Standard reactions were assembled following the teaching of Example 2. In addition, each of standard reactions contained 50 fmol (2 riM) phosphorylated TRAM second primer and 1 unit of T4 DNA ligase BRL. In addition, each set of standard reactions contained 500 fmol (20 nM) first primer P2 (Set A), P2.1 (Set B), or P2.2 (Set C). Reactions from each set of conditions contained $10^4$ molecules of an RNA template, which was generated following the teaching of Example 1. The reactions were incubated at 40° C. for 90 minutes. A portion of each incubated reaction was treated with DNase I to remove any residual primers. Serial 100-fold dilutions to $10^8$ were prepared for both DNase I treated and untreated portions of both NASBA™ and TRAM reactions.

Standard reactions were assembled following the teaching of Example 2. No primers were added to the standard reactions. Duplicate reactions contained 2-µl aliquots of the $10^4$, $10^6$ or $10^8$ dilutions of the DNase I treated or untreated portions of the sets of TRAM reactions were performed using the various first primers. One reaction from each set contained no added template. The reactions were incubated at 40° C. for 90 minutes.

Aliquots (5 µl) of the reactions were analyzed by agarose gel electrophoresis and blot hybridization following the teaching of Example 2. Visualization of the ethidium bromide stained products (FIG. 21) and autoradiography of the specifically hybridized products (FIG. 22) indicates that for TRAM RNA products amplified using the P2 first primer (Set A), reamplification in the absence of primers was consistently observed only at the $10^4$ dilution (cf. Set A of FIGS. 17 and 18).

Figure 21:
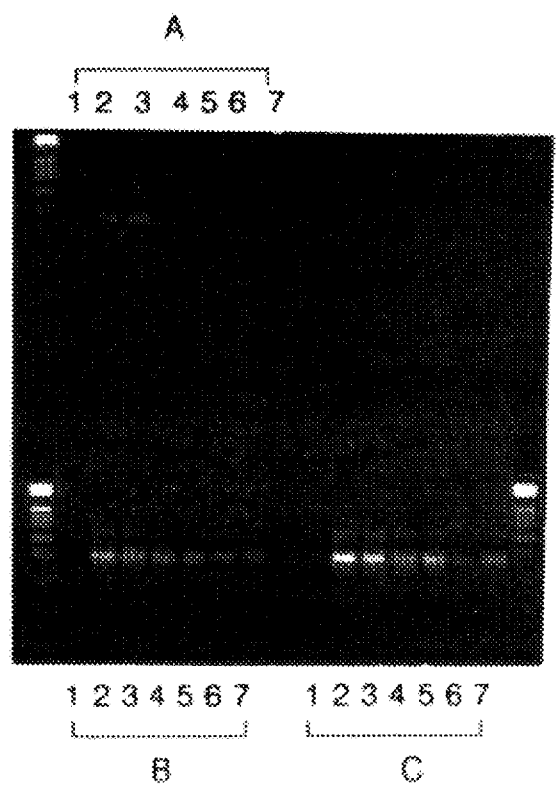
FIGS. 21 and 22 show the use of first primers with 5'-terminal stem-loop structures for cyclic amplification in TRAM in the absence of primers.
Figure 22:
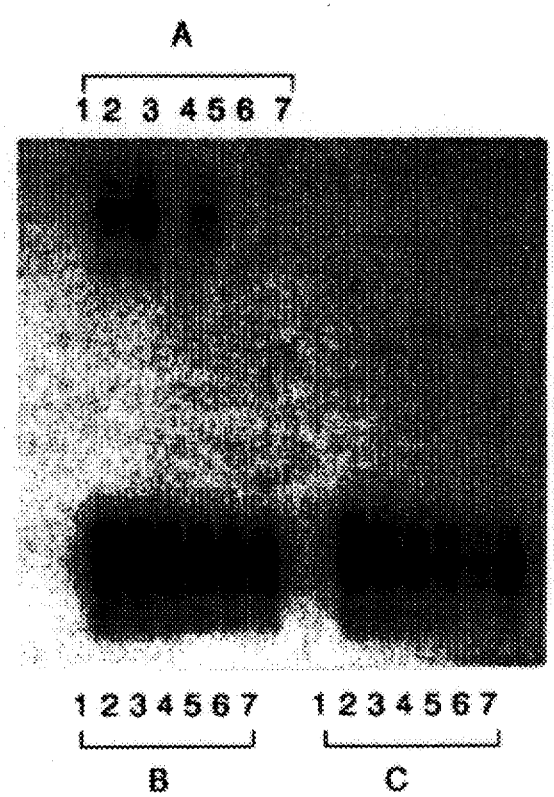

In FIGS. 21 and 22, the following lanes contain the following materials,

1—no added template 2,3—$10^{-4}$ dilution of primary TRAM reaction 4,5—$10^{-6}$ dilution of primary TRAM reaction 6,7—$10^{-8}$ dilution of primary TRAM reaction A—first primer (P2)

B—first primer (P2.1)

C—first primer (P2.2)

Conversely, TRAM RNA products amplified using either P2.1 (Set B) or P2.2 (Set C) as first primer could be reamplified in the absence of primers down to a $10^8$ dilution. Of the latter two first primers, P2.2 with a smaller stem-loop structure appears to generate an RNA product that can be more efficiently amplified in the absence of primers. It is contemplated that further optimization could be performed on the 5'-terminal sequence of the first primer to further improve the self-priming efficiency of the amplified RNA product. Thus, first primers with 5'-terminal sequences that can fold into stem-loop structures can be used to amplify RNA products with 3'-terminal priming sequences. Once formed, these RNA first templates with 3'-terminal priming sequences can be amplified in a cyclic process without primers.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

REFERENCES

1. EP 0427 073 A2 (Dattagupta).
2. EP 0427 074 A2 (Dattagupta).
3. Hattori, M and Y. Sakaki. 1986. Dideoxy sequencing method using denatured plasmid templates. Anal. Biochem. 152:232.
4. Holmes, D. S. and M. Quigley. 1981. A rapid boiling method for the preparation of bacterial plasmids. Anal. Biochem. 114:193.
5. Maniatis, T., E. Fritsch and J. Sambrook. 1982. Molecular Cloning: A laboratory manual Cold Spring Harbor Laboratory Cold Spring Harbor. N.Y. pp 170.
6. Miller, J. H. 1972. Experimentals in Molecular genetics Cold Spring Harbor Laboratory. Cold Spring Harbor. N.Y. pp 433.
7. Mullis, K. B., F. Faloona, S. Scharf, R. Saiki, G. Horn and H. Frlich. 1986. Specific enzymatic amplification of DNA in vitro: The polymerase chain reaction. Cold Spring Harbor Symp. Quant. Biol. 51:263.
8. Saiki, R. K., D. H. Gelfand, S. Stoffel, S. J. Scharf, R. Higuchi, G. T. Horn, K. B. Mullis and H. A. Frlich. 1988. Primer-directed enzymatic amplification of DNA with a thermostable DNA polymerase. Science 239:487.
9. Sanger, F., S. Nickden and A. R. Coulson. 1977. DNA sequencing with chain terminating inhibitors. Proc. Natl. Acad. Sci. USA 74:5463.
10. U.S. Pat. No. 4,683,202 (Mullis).
11. U.S. Pat. No. 4,683,195 (Saiki).
12. U.S. Ser. No. 080479 (Burg.), abandoned.
13. U.S. Pat. No. 5,130,238 (Malek).
14. U.S. Ser. No. 07/211,384 (Malek), now U.S. Pat. No. 5,409,818.
15. U.S. Ser. No. 08/275,250 (Sooknanan).
16. U.S. Pat. No. WO 91/18155 (Berninger).

We claim:

1. A process for the amplification of a specific nucleic acid sequence at a relatively constant temperature and without serial addition of reagents, comprising the steps of:
   (A) providing a single reaction medium containing reagents comprising:
      (i) a first oligonucleotide primer;
      (ii) an RNA polymerase;
      (iii) a DNA polymerase;
      (iv) a ribonuclease that hydrolyses RNA of an RNA-DNA hybrid without hydrolysing single- or double-stranded RNA or DNA;
      (v) ribonucleoside and deoxyribonucleoside triphosphates;
      (vi) a DNA ligase;
      (vii) a second oligonucleotide primer comprising a 3'-terminal priming sequence that is complementary to the specific nucleic acid sequence, minus-sense sequences of a promoter and an initiation site that are recognized by said RNA polymerase, a 5'-terminal sequence that is self-complementary to said minus-sense sequence of said initiation site, and a 5'-terminal phosphate group; and
      (viii) a single-stranded RNA comprising said specific nucleic acid sequence:
   (B) maintaining conditions such that
      (i) said second oligonucleotide primer hybridizes to said single-stranded RNA;
      (ii) said DNA polymerase uses said single-stranded RNA as a template to synthesize a complementary DNA by extension of said second oligonucleotide primer and thereby forms an RNA-DNA hybrid;
      (iii) said ribonuclease hydrolyses RNA which comprises said RNA-DNA hybrid;
      (iv) said first oligonucleotide primer hybridizes to said complementary DNA;
      (v) said DNA polymerase uses said complementary DNA as template to synthesize a DNA segment which terminates at said second oligonucleotide primer by extension of said first oligonucleotide primer;
      (v) said DNA ligase joins said DNA segment to said second oligonucleotide primer and thereby forms a DNA second template; and
      (vi) said RNA polymerase recognizes said promoter and transcribes said DNA second template,
   thereby providing copies of an RNA first template which comprises a sequence complementary to said specific nucleic acid sequence, minus-sense sequences of said promoter and said initiation site, and a 5'-terminal sequence that is self-complementary to said minus-sense sequence of said initiation site, and
   (C) maintaining conditions such that a cycle ensues wherein:
      (i) said first oligonucleotide primer hybridizes to said RNA first template;
      (ii) said DNA polymerase uses said RNA first template to synthesize a DNA second template by extension of said first oligonucleotide primer and thereby forms as RNA-DNA hybrid, said DNA second template comprising plus-sense sequences of said promoter and said initiation site, and a 3'-terminal priming sequence that is self-complementary to said plus-sense sequence of said initiation site;
      (iii) said ribonuclease hydrolyses RNA which comprises said RNA-DNA hybrid;
      (iv) said 3'-terminal priming sequence of said DNA second template hybridizes to said plus-sense sequence of said initiation site;

33

(v) said DNA polymerase uses said DNA second template as template to synthesize said promoter by extension of said DNA second template; and (vi) said RNA polymerase recognizes said promoter and transcribes said DNA second template, thereby providing copies of said RNA first template; and thereafter, (D) maintaining conditions such that a cycle ensues for a time sufficient to achieve a desired amplification of said specific nucleic acid sequence.

2. A process for the amplification of a specific nucleic acid sequence at a relatively constant temperature and without serial addition of reagents, comprising the steps of:

(A) providing a single reaction medium containing reagents comprising;
   (i) a first oligonucleotide primer;
   (ii) an RNA polymerase;
   (iii) a DNA polymerase;
   (iv) a ribonuclease that hydrolyses RNA of an RNA-DNA hybrid without hydrolysing single- or double-stranded RNA or DNA;
   (v) ribonucleoside and deoxyribonucleoside triphosphates;
   (vi) a DNA ligase;
   (vii) a second oligonucleotide primer comprising a 3'-terminal priming sequence that is complementary to the specific nucleic acid sequence, minus-sense sequences of a promoter and an initiation site that are recognized by said RNA polymerase, a 5'-terminal sequence that is self-complementary to said minus-sense sequence of said initiation site, and a 5'-terminal phosphate group; and
   (x) a single-stranded DNA comprising said specific nucleic acid sequence;

(B) maintaining conditions such that
   (i) said second oligonucleotide primer hybridizes to said single-stranded DNA;
   (ii) said DNA polymerase uses said single-stranded DNA as a template to synthesize a complementary DNA by extension of said second oligonucleotide primer and thereby forms a DNA-DNA hybrid;
   (iii) said DNA-DNA hybrid is denatured;
   (vi) said first oligonucleotide primer hybridizes to said complementary DNA;
   (v) said DNA polymerase uses said complementary DNA as template to synthesize a DNA segment which terminates at said second oligonucleotide primer by extension of said first oligonucleotide primer;
   (vi) said DNA ligase joins said DNA segment to said second oligonucleotide primer and thereby forms a DNA second template; and
   (vii) said RNA polymerase recognizes said promoter and transcribes said DNA second template, thereby providing copies of an RNA first template which comprises a sequence complementary to said specific nucleic acid sequence, minus-sense sequences of said promoter and said initiation site, and a 5'-terminal sequence that is self-complementary to at least said minus-sense sequence of said initiation site;

(C) maintaining conditions such that a cycle ensues wherein:
   (i) said first oligonucleotide primer hybridizes to said RNA first template;
   (ii) said DNA polymerase uses said RNA first template to synthesize a DNA second template by extension of

34 said first oligonucleotide primer and thereby forms as RNA-DNA hybrid, said DNA second template comprising plus-sense sequences of said promoter and said initiation site, and a 3'-terminal priming sequence that is self-complementary to said plus-sense sequence of said initiation site;
   (iii) said ribonuclease hydrolyses RNA which comprises said RNA-DNA hybrid;
   (iv) said 3'-terminal priming sequence of said DNA second template hybridizes to said plus-sense sequence of said initiation site;
   (v) said DNA polymerase uses said DNA second template as template to synthesize said promoter by extension of said DNA second template; and
   (vi) said RNA polymerase recognizes said promoter and transcribes said DNA second template, thereby providing copies of said RNA first template;

and thereafter, (D) maintaining conditions such that a cycle ensues for a time sufficient to achieve a desired amplification of said specific nucleic acid sequence.

3. A process according to claim 2, further comprising prior to step (A), denaturing double-stranded DNA to provide single-stranded DNA.

4. A process for the amplification of a specific nucleic acid sequence at a relatively constant temperature and without serial addition of reagents, comprising the steps of:

(A) providing a single reaction medium containing reagents comprising;
   (i) a first oligonucleotide primer;
   (ii) an RNA polymerase;
   (iii) a DNA polymerase;
   (iv) a ribonuclease that hydrolyses RNA of an RNA-DNA hybrid without hydrolysing single- or double-stranded RNA or DNA;
   (v) ribonucleoside and deoxyribonucleoside triphosphates;
   (vi) a second oligonucleotide primer comprising a 3'-terminal priming sequence that is complementary to the specific nucleic acid sequence, minus-sense sequences of a promoter and an initiation site that are recognized by said RNA polymerase, a 5'-terminal sequence that is self-complementary to said minus-sense sequence of said initiation site, and further comprising a 5'-terminal oligoribonucleotide segment; and
   (x) a single-stranded RNA comprising said specific nucleic acid sequence;

(B) maintaining conditions such that:
   (i) said second oligonucleotide primer hybridizes to said single-stranded RNA;
   (ii) said DNA polymerase uses said single-stranded RNA as a template to synthesize a complementary DNA by extension of said second oligonucleotide primer and thereby forms an RNA-DNA hybrid;
   (iii) said ribonuclease hydrolyses RNA which comprises said RNA-DNA hybrid;
   (iv) said first oligonucleotide primer hybridizes to said complementary DNA;
   (v) said DNA polymerase uses said complementary DNA as template to synthesize a DNA strand;
   (vi) said ribonuclease hydrolyses RNA of said second primer within said complementary DNA;
   (vii) the 3'-end of said DNA strand hybridizes to a complementary sequence of said DNA strand thereby forming a 3'-stem loop structure;
   (viii) said DNA polymerase extends said 3'-end of said DNA strand to provide said promoter;

(vi) said RNA polymerase recognizes said promoter and transcribes said DNA second template, thereby providing copies of an RNA first template which comprises a sequence complementary to said specific nucleic acid sequence, minus-sense sequence of said promoter and said initiation site, and a 5'-terminal sequence that is self-complementary to at least said minus-sense sequence of said initiation site;

(C) maintaining conditions such that a cycle ensues wherein:
   (i) said first oligonucleotide primer hybridizes to said RNA first template;
   (ii) said DNA polymerase uses said RNA first template to synthesize a DNA second template by extension of said first oligonucleotide primer and thereby forms as RNA-DNA hybrid, said DNA second template comprising plus-sense sequences of said promoter and said initiation site, and a 3'-terminal priming sequence that is self-complementary to said plus-sense sequence of said initiation site;
   (iii) said ribonuclease hydrolyses RNA which comprises said RNA-DNA hybrid;
   (iv) said 3'-terminal priming sequence of said DNA second template hybridizes to said plus-sense sequence of said initiation site;
   (v) said DNA polymerase uses said DNA second template as template to synthesize said promoter by extension of said DNA second template; and
   (vi) said RNA polymerase recognizes said promoter and transcribes said DNA second template, thereby providing copies of said RNA first template; and thereafter, (D) maintaining conditions such that a cycle ensues for a time sufficient to achieve a desired amplification of said specific nucleic acid sequence.

5. A process for the amplification of a specific nucleic acid sequence at a relatively constant temperature and without serial addition of reagents, comprising the steps of:

(A) providing a single reaction medium containing reagents comprising;
   (i) a first oligonucleotide primer;
   (ii) an RNA polymerase;
   (iii) a DNA polymerase;
   (iv) a ribonuclease that hydrolyses RNA of an RNA-DNA hybrid without hydrolysing single- or double-stranded RNA or DNA;
   (v) ribonucleoside and deoxyribonucleoside triphosphates;
   (vi) a DNA ligase; and
   (vii) a single-stranded DNA which comprises a sequence complementary to said specific nucleic acid sequence, minus-sense sequences of a promoter and an initiation site that are recognized by said RNA polymerase, a 5'-terminal sequence that is self-complementary to said minus-sense sequence of said initiation site, and a 5'-terminal phosphate group (B) maintaining conditions such that:
   (i) said first oligonucleotide primer hybridizes to said single-stranded DNA;
   (ii) said DNA polymerase uses said single-stranded DNA as a template to synthesize a DNA segment which terminates at said 5'-terminal sequence by extension of said first oligonucleotide primer;
   (iii) said DNA ligase joins said DNA segment to said single-stranded DNA and thereby forms a DNA second template; and (iv) said RNA polymerase recognizes said promoter and transcribes said DNA second template, thereby providing copies of an RNA first template which comprises a sequence complementary to said specific nucleic acid sequence, minus-sense sequence of said promoter and said initiation site, and a 5'-terminal sequence that is self-complementary to at least said minus-sense sequence of said initiation site:

(C) maintaining conditions such that a cycle ensues wherein:
   (i) said first oligonucleotide primer hybridizes to said RNA first template;
   (ii) said DNA polymerase uses said RNA first template to synthesize a DNA second template by extension of said first oligonucleotide primer and thereby forms as RNA-DNA hybrid, said DNA second template comprising plus-sense sequences of said promoter and said initiation site, and a 3'-terminal priming sequence that is self-complementary to said plus-sense sequence of said initiation site;
   (iii) said ribonuclease hydrolyses RNA which comprises said RNA-DNA hybrid;
   (iv) said 3'-terminal priming sequence of said DNA second template hybridizes to said plus-sense sequence of said initiation site:
   (v) said DNA polymerase uses said DNA second template as template to synthesize said promoter by extension of said DNA second template; and
   (vi) said RNA polymerase recognizes said promoter and transcribes said DNA second template, thereby providing copies of said RNA first template;

and thereafter, (D) maintaining conditions such that a cycle ensues for a time sufficient to achieve a desired amplification of said specific nucleic acid sequence.

6. A process according to claim 5, wherein step (B) further comprises adding to said reaction medium an RNA-DNA hybrid comprising said single-stranded DNA, such that said ribonuclease hydrolyses RNA which comprises said RNA-DNA hybrid.

7. A process for the amplification of a specific nucleic acid sequence at a relatively constant temperature and without serial addition of reagents, comprising the steps of:

(A) providing a single reaction medium containing reagents comprising;
   (i) an RNA polymerase;
   (ii) a DNA polymerase;
   (iii) a ribonuclease that hydrolyses RNA of an RNA-DNA hybrid without hydrolysing single- or double-stranded RNA or DNA;
   (iv) ribonucleoside and deoxyribonucleoside triphosphates;
   (v) a DNA ligase;
   (vi) a first oligonucleotide primer comprising a 5' complementary sequence;
   (vii) a second oligonucleotide primer comprising a 3'-terminal priming sequence that is complementary to the specific nucleic acid sequence, minus-sense sequences of a promoter and an initiation site that are recognized by said RNA polymerase, a 5'-terminal sequence that is self-complementary to said minus-sense sequence of said initiation site, and a 5'-terminal phosphate group; and
   (viii) a single-stranded RNA comprising said specific nucleic acid sequence:

(B) maintaining conditions such that
   (i) said second oligonucleotide primer hybridizes to said single-stranded RNA;
   (ii) said DNA polymerase uses said single-stranded RNA as a template to synthesize a complementary DNA by extension of said second oligonucleotide primer and thereby forms an RNA-DNA hybrid;
   (iii) said ribonuclease hydrolyses RNA which comprises said RNA-DNA hybrid;
   (iv) said first oligonucleotide primer hybridizes to said complementary DNA;
   (v) said DNA polymerase uses said complementary DNA as template to synthesize a DNA segment which terminates at said second oligonucleotide primer by extension of said first oligonucleotide primer;
   (vi) said DNA ligase joins said DNA segment to said second oligonucleotide primer and thereby forms a DNA second template; and
   (vii) said RNA polymerase recognizes said promoter and transcribes said DNA second template, thereby providing copies of an RNA first template which comprises a sequence complementary to said specific nucleic acid sequence, minus-sense sequences of said promoter and said initiation site, and a 5'-terminal sequence that is self-complementary to said minus-sense sequence of said initiation site and a 3'-terminal priming sequence that hybridizes to a complementary sequence of the RNA first template thereby forming an RNA:RNA stem loop, and (C) maintaining conditions such that a cycle ensues wherein:
   (i) said DNA polymerase uses said RNA first template to synthesize a DNA second template by extension of said 3'-terminal priming sequence and thereby forms an RNA-DNA hybrid, said DNA second template comprising plus-sense sequences of said promoter and said initiation site, and a 3'-terminal priming sequence that is self-complementary to said plus-sense sequence of said initiation site;
   (ii) said ribonuclease hydrolyses RNA which comprises said RNA-DNA hybrid but not RNA of said RNA-RNA stem loop;
   (iii) said 3'-terminal priming sequence of said DNA second template hybridizes to said plus-sense sequence of said initiation site;
   (iv) said DNA polymerase uses said DNA second template as template to synthesize said promoter by extension of said DNA second template; and
   (v) said RNA polymerase recognizes said promoter and transcribes said DNA second template, thereby providing copies of said RNA first template;

and thereafter, (D) maintaining said conditions for a time sufficient to achieve a desired amplification of said specific nucleic acid sequence.

8. A process for the amplification of a specific nucleic acid sequence at a relatively constant temperature and without serial addition of reagents, comprising the steps of:
(A) providing a single reaction medium containing reagents comprising;
   (i) an RNA polymerase;
   (ii) a DNA polymerase;
   (iii) a ribonuclease that hydrolyses RNA of an RNA-DNA hybrid without hydrolysing single- or double-stranded RNA or DNA;
   (iv) ribonucleoside and deoxyribonucleoside triphosphates;
   (v) a DNA ligase;
   (vi) a first oligonucleotide primer comprising a 5' complementary sequence;
   (vii) a second oligonucleotide primer comprising a 3'-terminal priming sequence that is complementary to the specific nucleic acid sequence, minus-sense sequences of a promoter and an initiation site that are recognized by said RNA polymerase, a 5'-terminal sequence that is self-complementary to said minus-sense sequence of said initiation site, and a 5'-terminal phosphate group; and
   (x) a single-stranded DNA comprising said specific nucleic acid sequence;
(B) under conditions such that
   (i) said second oligonucleotide primer hybridizes to said single-stranded DNA;
   (ii) said DNA polymerase uses said single-stranded DNA as a template to synthesize a complementary DNA by extension of said second oligonucleotide primer and thereby forms a DNA-DNA hybrid;
   (iii) said DNA-DNA hybrid is denatured;
   (vi) said first oligonucleotide primer hybridizes to said complementary DNA;
   (v) said DNA polymerase uses said complementary DNA as template to synthesize a DNA segment which terminates at said second oligonucleotide primer by extension of said first oligonucleotide primer;
   (vi) said DNA ligase joins said DNA segment to said second oligonucleotide primer and thereby forms a DNA second template; and
   (vii) said RNA polymerase recognizes said promoter and transcribes said DNA second template, thereby providing copies of an RNA first template which comprises a sequence complementary to said specific nucleic acid sequence, minus-sense sequences of said promoter and said initiation site, and a 5'-terminal sequence that is self-complementary to at least said minus-sense sequence of said initiation site and a 3'-terminal priming sequence that hybridizes to a complementary sequence of the RNA first template thereby forming an RNA:RNA stem loop;

(C) maintaining conditions such that a cycle ensues wherein:
   (i) said DNA polymerase uses said RNA first template to synthesize a DNA second template by extension of said 3'-terminal priming sequence and thereby forms an RNA-DNA hybrid, said DNA second template comprising plus-sense sequences of said promoter and said initiation site, and a 3'-terminal priming sequence that is self-complementary to said plus-sense sequence of said initiation site;
   (ii) said ribonuclease hydrolyses RNA which comprises said RNA-DNA hybrid but not RNA of said RNA-RNA stem loop;
   (iii) said 3'-terminal priming sequence of said DNA second template hybridizes to said plus-sense sequence of said initiation site;
   (iv) said DNA polymerase uses said DNA second template as template to synthesize said promoter by extension of said DNA second template; and
   (v) said RNA polymerase recognizes said promoter and transcribes said DNA second template, thereby providing copies of said RNA first template;

and thereafter, (D) maintaining said conditions for a time sufficient to achieve a desired amplification of said specific nucleic acid sequence.

9. A process for the amplification of a specific nucleic acid sequence at a relatively constant temperature and without serial addition of reagents, comprising the steps of:

(A) providing a single reaction medium containing reagents comprising;
  (i) an RNA polymerase;
  (ii) a DNA polymerase;
  (iii) a ribonuclease that hydrolyses RNA of an RNA-DNA hybrid without hydrolysing single- or double-stranded RNA or DNA;
  (iv) ribonucleoside and deoxyribonucleoside triphosphates;
  (v) a first oligonucleotide primer comprising a 5' complementary sequence;
  (vi) a second oligonucleotide primer comprising a 3'-terminal priming sequence that is complementary to the specific nucleic acid sequence, minus-sense sequences of a promoter and an initiation site that are recognized by said RNA polymerase, a 5'-terminal sequence that is self-complementary to said minus-sense sequence of said initiation site, and further comprising a 5'-terminal oligoribonucleotide segment; and
  (x) a single-stranded RNA comprising said specific nucleic acid sequence:

(B) under conditions such that:
  (i) said second oligonucleotide primer hybridizes to said single-stranded RNA;
  (ii) said DNA polymerase uses said single-stranded RNA as a template to synthesize a complementary DNA by extension of said second oligonucleotide primer and thereby forms an RNA-DNA hybrid;
  (iii) said ribonuclease hydrolyses RNA which comprises said RNA-DNA hybrid;
  (iv) said first oligonucleotide primer hybridizes to said complementary DNA;
  (v) said DNA polymerase uses said complementary DNA as template to synthesize a DNA strand;
  (vi) said ribonuclease hydrolyses RNA of said second primer within said complementary DNA;
  (vii) the 3'-end of said DNA strand hybridizes to a complementary sequence of said DNA strand thereby forming a 3'-stem loop structure;
  (viii) said DNA polymerase extends said 3'-end of said DNA strand to provide said promoter;
  (vi) said RNA polymerase recognizes said promoter and transcribes said DNA second template, thereby providing copies of an RNA first template which comprises a sequence complementary to said specific nucleic acid sequence, minus-sense sequence of said promoter and said initiation site, and a 5'-terminal sequence that is self-complementary to at least said minus-sense sequence of said initiation site and a 3'-terminal priming sequence that hybridizes to a complementary sequence of the RNA first template thereby forming an RNA:RNA stem loop;

(C) maintaining conditions such that a cycle ensues wherein:
  (i) said DNA polymerase uses said RNA first template to synthesize a DNA second template by extension of said 3'-terminal priming sequence and thereby forms an RNA-DNA hybrid, said DNA second template comprising plus-sense sequences of said promoter and said initiation site, and a 3'-terminal priming sequence that is self-complementary to said plus-sense sequence of said initiation site;
  (ii) said ribonuclease hydrolyses RNA which comprises said RNA-DNA hybrid but not RNA of said RNA-RNA stem loop;
  (iii) said 3'-terminal priming sequence of said DNA second template hybridizes to said plus-sense sequence of said initiation site;
  (iv) said DNA polymerase uses said DNA second template as template to synthesize said promoter by extension of said DNA second template; and
  (v) said RNA polymerase recognizes said promoter and transcribes said DNA second template, thereby providing copies of said RNA first template;

and thereafter, (D) maintaining said conditions for a time sufficient to achieve a desired amplification of said specific nucleic acid sequence.

10. A process according to claim 1, wherein said RNA polymerase is bateriophase T7 RNA polymerase and wherein said minus-sense sequence of said initiation site and said minus-sense sequence of said promoter together comprise the nucleotide sequence complementary to 5'-AATTCTAATACGACTCACTATAGGGAGA-3' (nucleotides 1–28 of SEQ ID NO: 5).

11. A process according to claim 1, wherein said process further comprises, after step (D), a step (E) of monitoring said reaction medium for consumption of any of said reagents or for accumulation of any product of said cycle.

12. A process according to claim 1 wherein said ribonuclease comprises calf thymus ribonuclease H.

13. A process according to claim 1, wherein said RNA polymerase is a bacteriophage RNA polymerase.

14. A process according to claim 13, wherein said bacteriophage RNA polymerase is selected from the group consisting of bacteriophage T7 RNA polymerase, bacteriophage T3 polymerase, bacteriophage φII polymerase, *Salmonella* bacteriophage sp6 polymerase, and *Pseudomonas* bacteriophage gh-1 polymerase.

15. A process according to claim 1, wherein said DNA polymerase is a retrovirus reverse transcriptase.

16. A process according to claim 15, wherein said retrovirus reverse transcriptase is selected from the group consisting of avian myeloblastosis virus polymerase, and a Moloney murine leukaemia virus polymerase.

17. A process according to claim 1, wherein said DNA polymerase lacks exonuclease activity.

18. A process according to claim 1, wherein all DNA polymerases in said reaction medium lack exonuclease and DNA endonuclease activity.

19. A process according to claim 1, wherein said DNA polymerase is selected from the group consisting of avian myeloblastosis virus polymerase, DNA polymerase β, and calf thymus DNA polymerase.

20. A process according to claim 1, wherein step (C) comprises maintaining said conditions for a time between 30 minutes and 4 hours.

21. A process according to claim 1, further comprising the steps of ligating a DNA product of said cycle into a cloning vector and then cloning said DNA product.

22. A process according to claim 21, further comprising the step of expressing a product encoded by said DNA product of said cycle in an expression system.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

TCTCCCTATA GTGAGTCGTA TTA    23

( 2 ) INFORMATION FOR SEQ ID NO:2:

( i ) SEQUENCE CHARACTERISTICS:
( A ) LENGTH: 134 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:2:

AGACAAGAUA GAGGAAGAGC AAAACAAAAG UAAGAAAAA GCACAGCAAG CAGCAGGGCA    60

UGCAGGGCCU AUUGCACCAG GCCAGAUGAG AGAACCAAGG GGAAGUGACA UAGCAGGAAC    120

UACUAGUACC CUUC    134

( 2 ) INFORMATION FOR SEQ ID NO:3:

( i ) SEQUENCE CHARACTERISTICS:
( A ) LENGTH: 134 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

| | | | | | |
|---|---|---|---|---|---|
| GAAGGGTACT | AGTAGTTCCT | GCTATGTCAC | TTCCCCTTGG | TTCTCTCATC | TGGCCTGGTG | 60
| CAATAGGCCC | TGCATGCCCT | GCTGCTTGCT | GTGCTTTTTT | CTTACTTTTG | TTTGCTCTT | 120
| CCTCTATCTT | GTCT | | | | | 134

( 2 ) INFORMATION FOR SEQ ID NO:4:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

| | | | | | |
|---|---|---|---|---|---|
| GGGAGATTTA | ACTCAGACGG | GTGTTAAATC | TCCCTATAGT | GAGTCGTATT | AGAATTGAAG | 60
| GGTACTAGTA | GTTCCTGC | | | | | 78

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

AATTCTAATA CGACTCACTA TAGGGAGAAG GGTACTAGTA GTTCCTGC          48

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

AGACAAGATA GAGGAAGAGC A          21

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CCAGGCCAGA TGAGAGAACC AAGGGGAAG          29

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single

```
            ( D ) TOPOLOGY: linear ( i i ) MOLECULE TYPE: DNA ( x i ) SEQUENCE DESCRIPTION: SEQ ID NO:8:

AGACAAGATA GAGGAAGAGC A                                                         2 1

( 2 ) INFORMATION FOR SEQ ID NO:9:

( i ) SEQUENCE CHARACTERISTICS:
                ( A ) LENGTH: 44 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:9:

TACTCATGCT GAGTCCATGA GTAAGACAAG ATAGAGGAAG AGCA                                 4 4

( 2 ) INFORMATION FOR SEQ ID NO:10:

( i ) SEQUENCE CHARACTERISTICS:
                ( A ) LENGTH: 30 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:10:

TACTGAGTAA GACAAGATAG AGGAAGAGCA                                                 3 0
```